US010561304B2

(12) United States Patent
Ishikawa et al.

(10) Patent No.: US 10,561,304 B2
(45) Date of Patent: Feb. 18, 2020

(54) MEDICAL STEREOSCOPIC OBSERVATION DEVICE, MEDICAL STEREOSCOPIC OBSERVATION METHOD, AND PROGRAM

(71) Applicant: Sony Olympus Medical Solutions Inc., Tokyo (JP)

(72) Inventors: Tomonori Ishikawa, Tokyo (JP); Masataka Kado, Kanagawa (JP); Hiroshi Ushiroda, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 15/573,561

(22) PCT Filed: Mar. 28, 2016

(86) PCT No.: PCT/JP2016/059856
§ 371 (c)(1),
(2) Date: Nov. 13, 2017

(87) PCT Pub. No.: WO2016/208246
PCT Pub. Date: Dec. 29, 2016

(65) Prior Publication Data
US 2018/0125340 A1 May 10, 2018

(30) Foreign Application Priority Data
Jun. 24, 2015 (JP) ................................. 2015-126228

(51) Int. Cl.
*A61B 1/04* (2006.01)
*A61B 90/20* (2016.01)
(Continued)

(52) U.S. Cl.
CPC ................ *A61B 1/04* (2013.01); *A61B 90/20* (2016.02); *H04N 13/106* (2018.05); *H04N 13/20* (2018.05); *G03B 35/08* (2013.01)

(58) Field of Classification Search
CPC ....... A61B 1/04; A61B 90/20; A61B 1/00006; A61B 1/00009; A61B 1/00193;
(Continued)

(56) References Cited

U.S. PATENT DOCUMENTS 6,005,607 A 12/1999 Uomori et al.
6,175,379 B1 1/2001 Uomori et al.
(Continued)

FOREIGN PATENT DOCUMENTS

CN 1313712 A 9/2001
CN 1864415 A 11/2006
(Continued)

OTHER PUBLICATIONS

Extended European Search Report dated Nov. 6, 2018 in corresponding European Patent Application No. 16814017.6, 11 pages.
(Continued)

Primary Examiner — Chong Wu
(74) Attorney, Agent, or Firm — Xsensus LLP

(57) ABSTRACT

[Object] To present a three-dimensional image in a more favorable mode, regardless of differences in display conditions.
[Solution] A medical stereoscopic observation device including: an acquisition section that acquires input image data; a parallax control section that controls, for each of a plurality of different display regions, a parallax value in accordance with display size of the display region; and an image generation section that generates, for each display region, a parallax image corresponding to each of a plurality of viewpoints for display in the display region, on a basis of the acquired input image data and the parallax value corresponding to the display region.

12 Claims, 19 Drawing Sheets

(51) Int. Cl.
*H04N 13/20* (2018.01)
*H04N 13/106* (2018.01)
*G03B 35/08* (2006.01)

(58) Field of Classification Search
CPC .... A61B 1/045; H04N 13/106; H04N 13/128; H04N 13/20; G02B 23/2415; G03B 35/08
See application file for complete search history.

(56) References Cited

U.S. PATENT DOCUMENTS

| | | | |
|---|---|---|---|
| 6,268,880 | B1 | 7/2001 | Uomori et al. |
| 6,377,625 | B1* | 4/2002 | Kim .................... H04N 19/597 375/240.08 |
| 2001/0033327 | A1 | 10/2001 | Uomori et al. |
| 2002/0024592 | A1* | 2/2002 | Uomori ............... H04N 13/398 348/42 |
| 2006/0290778 | A1* | 12/2006 | Kitaura ............... H04N 13/128 348/51 |
| 2012/0098930 | A1 | 4/2012 | Yamaguchi |
| 2012/0320048 | A1 | 12/2012 | Yamashita et al. |
| 2013/0094833 | A1 | 4/2013 | Fujita |
| 2013/0170737 | A1 | 7/2013 | Arita et al. |
| 2013/0272677 | A1 | 10/2013 | Tsuda et al. |
| 2014/0022246 | A1 | 1/2014 | Ono et al. |

FOREIGN PATENT DOCUMENTS

| | | |
|---|---|---|
| EP | 1 328 129 A1 | 7/2003 |
| EP | 1 662 809 A1 | 5/2006 |
| JP | 9-121370 A | 5/1997 |
| JP | 2005-73049 A | 3/2005 |
| JP | 2012-85102 A | 4/2012 |
| JP | 2012-94936 A | 5/2012 |
| WO | 2011/108283 A1 | 9/2011 |
| WO | 2011/155212 A1 | 12/2011 |
| WO | 2012/137454 A1 | 10/2012 |

OTHER PUBLICATIONS

International Search Report dated Jun. 21, 2016 in PCT/JP2016/059856 filed Mar. 28, 2016.
Chinese Office Action dated Aug. 12, 2019, issued in corresponding Chinese Patent Application No. 2016800354037.

* cited by examiner

FIG. 14
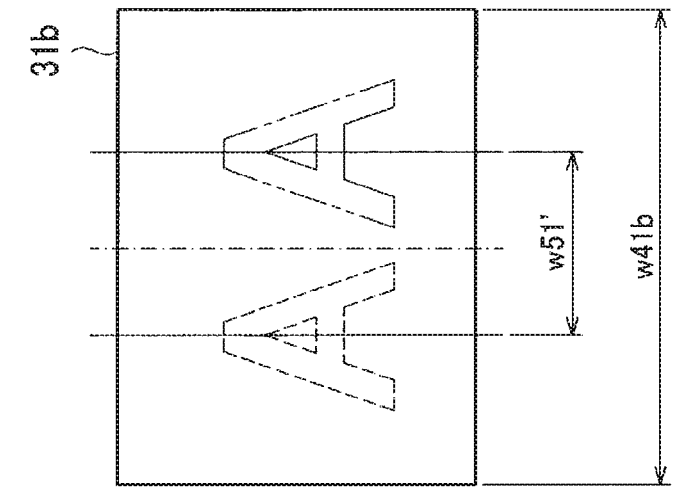
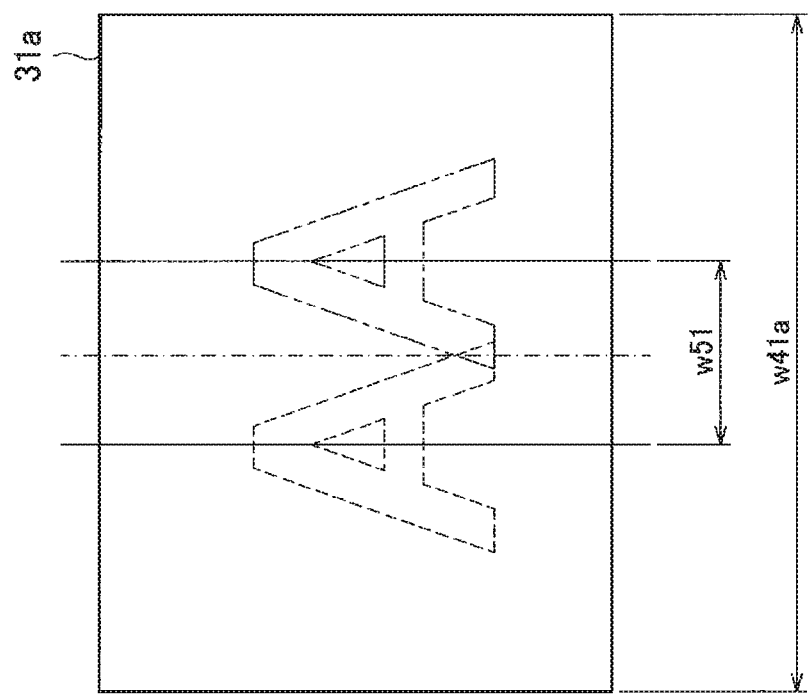

MEDICAL STEREOSCOPIC OBSERVATION DEVICE, MEDICAL STEREOSCOPIC OBSERVATION METHOD, AND PROGRAM

TECHNICAL FIELD

The present disclosure relates to a medical stereoscopic observation device, a medical stereoscopic observation method, and a program.

BACKGROUND ART

Recently, due to advancements in surgical techniques and surgical equipment, surgeries for performing various treatments (also called microsurgery) while observing an affected site with an observation device for medical use, such as a surgical microscope or an endoscope, are coming to be conducted frequently. Also, such observation devices for medical use are not limited to devices that enable optical observation of the affected area, and also include devices that display an image of the affected area captured by an imaging section (camera) or the like as an electronic image on a display such as a monitor.

In addition, when displaying, on a display, an image of an affected area captured by an imaging section of an observation device, the image often is displayed as a flat two-dimensional (2D) image. However, since a sense of perspective is difficult to obtain from a 2D image, and the relative distance between the affected area and a treatment tool may be difficult to grasp, in recent years, technology that displays a captured image of an affected area as a stereoscopic three-dimensional (3D) image has also been developed. For example, Patent Literature 1 discloses an example of technology for observing a three-dimensional image.

In this way, in an observation device that displays a captured image of an affected area as a stereoscopic three-dimensional (3D) image (hereinafter designated a "stereoscopic observation device" in some cases), for example, by causing the left and right eyes to observe different viewpoint images, the user is made to observe an image of the affected area as a stereoscopic three-dimensional image.

CITATION LIST

Patent Literature

Patent Literature 1: WO 2011/155212

DISCLOSURE OF INVENTION

Technical Problem

In addition, the circumstances in which a medical observation device as described above is used also includes cases in which various information should be checked, including images of an affected area. Under such circumstances, usage patterns such as displaying images respectively on multiple displays or displaying multiple images inside a display may also be anticipated. As a specific example, a case is anticipated in which an overall picture of the affected area is displayed on one display, while a magnified image of the affected area is displayed on another display. As another example, a case is also anticipated in which an image of the affected area is displayed on one display, while an image captured by another imaging device, such as a computed tomography (CT) image or a magnetic resonance imaging (MRI) image, is displayed on another display.

On the other hand, the display position in the depth direction of a three-dimensional image observed by a user is decided in accordance with a spacing between the images observed respectively by the left and right eyes (in other words, a parallax value set between the images). For this reason, the observed position in the depth direction changes in accordance with differences in the display conditions, such as differences in the size and resolution of the display section, for example, and the three-dimensional image is not necessarily observed in a favorable mode in some cases.

Accordingly, the present disclosure proposes a medical stereoscopic observation device, a medical stereoscopic observation method, and a program capable of presenting a three-dimensional image in a more favorable mode, regardless of differences in display conditions.

Solution to Problem

According to the present disclosure, there is provided a medical stereoscopic observation device including: an acquisition section that acquires input image data; a parallax control section that controls, for each of a plurality of different display regions, a parallax value in accordance with display size of the display region; and an image generation section that generates, for each display region, a parallax image corresponding to each of a plurality of viewpoints for display in the display region, on a basis of the acquired input image data and the parallax value corresponding to the display region.

In addition, according to the present disclosure, there is provided a medical stereoscopic observation method including: acquiring input image data; controlling, for each of a plurality of different display regions, a parallax value in accordance with display size of the display region; and generating, for each display region, a parallax image corresponding to each of a plurality of viewpoints for display in the display region, on a basis of the acquired input image data and the parallax value corresponding to the display region.

In addition, according to the present disclosure, there is provided a program causing a computer to execute: acquiring input image data; controlling, for each of a plurality of different display regions, a parallax value in accordance with display size of the display region; and generating, for each display region, a parallax image corresponding to each of a plurality of viewpoints for display in the display region, on a basis of the acquired input image data and the parallax value corresponding to the display region.

Advantageous Effects of Invention

According to the present disclosure as described above, there is provided a medical stereoscopic observation device, a medical stereoscopic observation method, and a program capable of presenting a three-dimensional image in a more favorable mode, regardless of differences in display conditions.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 14 is an explanatory diagram for explaining an overview of a medical stereoscopic observation system according to the embodiment.

MODE(S) FOR CARRYING OUT THE INVENTION

Figure 1:
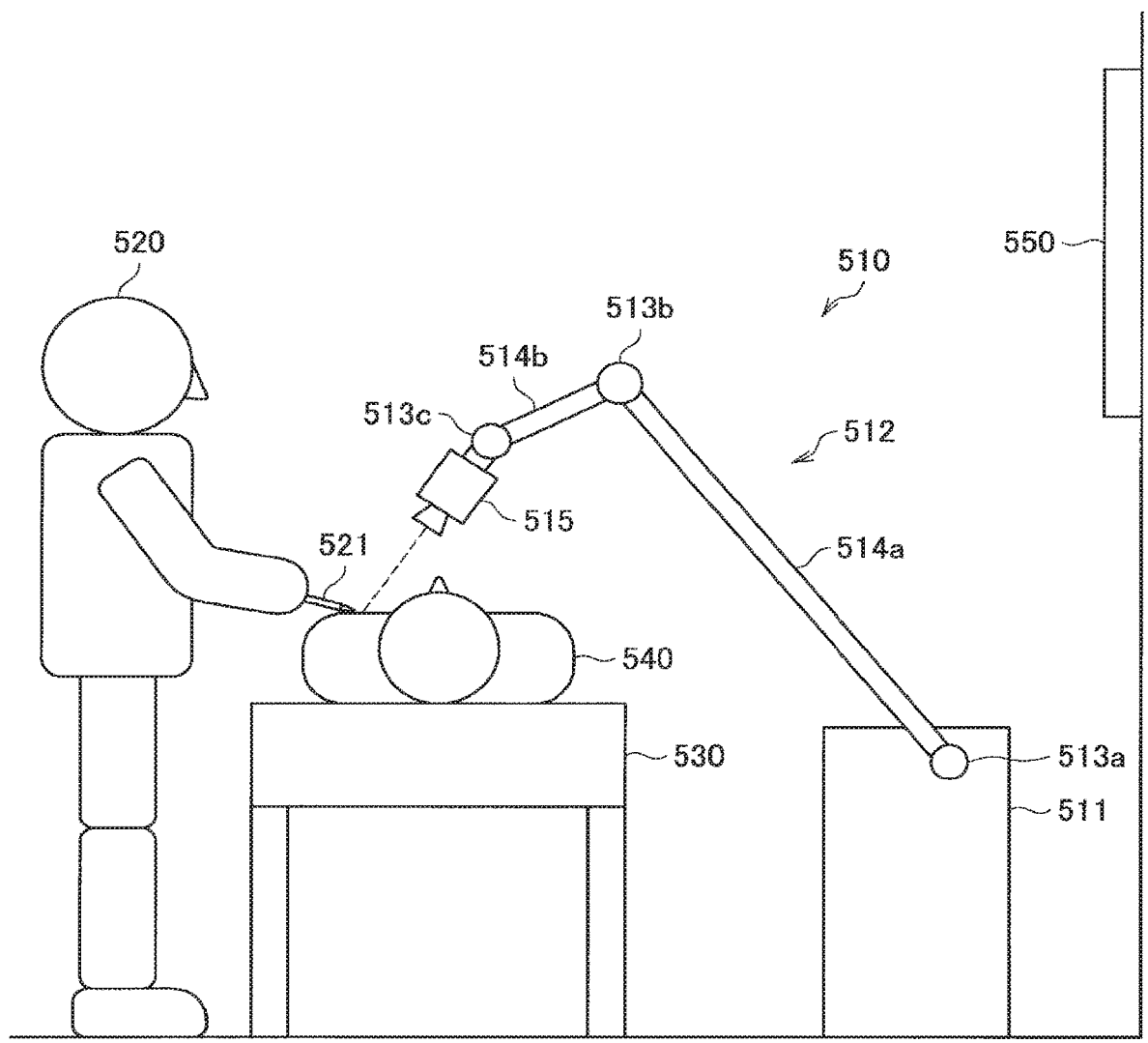
FIG. 1 is an explanatory diagram for explaining an applied example of a medical stereoscopic observation device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. Overview of medical stereoscopic observation device
    1.1. Applied example of medical stereoscopic observation device
    1.2. Exterior appearance of medical stereoscopic observation device
    1.3. Schematic functional configuration of medical stereoscopic observation system
2. Investigation of medical stereoscopic observation device
3. Functional configuration of image processing device
4. Flow of processes by image processing device
6. Modifications
    6.1. Modification 1: Example of control in association with electronic zoom
    6.2. Modification 2: Example of control in association with multi-screen display
    6.3. Modification 3: Presentation of field of view range
    6.4. Modification 4: Control according to viewing distance
7. Hardware configuration
8. Conclusion

1. Overview of Medical Stereoscopic Observation Device

[1.1. Applied Example of Medical Stereoscopic Observation Device]

First, to further elucidate the present disclosure, an applied example of a medical stereoscopic observation device according to an embodiment of the present disclosure will be described.

For example, FIG. 1 illustrates an example of a case for an applied example of using a medical stereoscopic observation device according to an embodiment of the present disclosure, in which a surgical video microscope device equipped with an arm is used as the medical stereoscopic observation device. FIG. 1 is an explanatory diagram for explaining an applied example of a medical stereoscopic observation device according to an embodiment of the present disclosure.

FIG. 1 diagrammatically illustrates how a medical procedure is performed using a surgical video microscope device according to the present embodiment. Specifically, referring to FIG. 9, a state is illustrated in which a physician acting as the surgeon (user) 520 is using a surgical tool 521, such as a scalpel, tweezers, or forceps, for example, to perform surgery on a subject (patient) 540 lying on an operating table 530. Note that in the following description, medical procedure is used as a collective term to denote various types of medical treatments performed by a physician acting as the user 520 on a patient acting as the subject 540, such as a surgery or an examination. Also, although the example illustrated in FIG. 1 illustrates a situation of surgery as an example of a medical procedure, the medical procedure in which the surgical video microscope device 510 is used is not limited to surgery, and may be any of various other types of medical procedures such as an examination using an endoscope.

Beside the operating table 530, the surgical video microscope device 510 according to the present embodiment is provided. The surgical video microscope device 510 is equipped with a base section 511 which acts as a base, an arm section 512 which extends from the base section 511, and an imaging unit 515 connected as a front edge unit on the front edge of the arm section 512. The arm section 512 includes multiple joint sections 513a, 513b, and 513c, multiple links 514a and 514b joined by the joint sections 513a and 513b, and the imaging unit 515 provided on the front edge of the arm section 512. In the example illustrated in FIG. 1, for the sake of simplicity, the arm section 512 includes three joint sections 513a to 513c and two links 514a and 514b, but in actuality, the degrees of freedom in the positions and the attitudes of the arm section 512 and the imaging unit 515 may be considered to appropriately configure factors such as the numbers and shapes of the joint sections 513a to 513c and the links 514a and 514b, and the directions of the drive shafts of the joints 513a to 513c, so as to achieve the desired degrees of freedom.

The joint sections 513a to 513c have a function of rotatably joining the links 514a and 514b to each other, and by driving the rotation of the joint sections 513a to 513c, the driving of the arm section 512 is controlled. Herein, in the following description, the position of each structural member of the surgical video microscope device 510 means the position (coordinates) in a space prescribed for drive control, while the attitude of each structural member means the direction (angle) with respect to an arbitrary axis in the space prescribed for drive control. Also, in the following description, the driving (or the drive control) of the arm section 512 refers to the driving (or the drive control) of the joint sections 513a to 513c, as well as to the position and attitude of each structural member of the arm section 512 being changed (or such change being controlled) by conducting the driving (or the drive control) of the joint sections 513a to 513c.

On the front edge of the arm section 512, the imaging unit 515 is connected as a front edge unit. The imaging unit 515 is a unit that acquires an image of an imaging target, and is a device such as a camera capable of capturing a moving image or a still image, for example. As illustrated in FIG. 1, the attitudes and the positions of the arm section 512 and the imaging unit 515 are controlled by the surgical video microscope device 510 so that the imaging unit 515 provided on the front edge of the arm section 512 captures the operating site of the subject 540. Note that the configuration of the imaging unit 515 connected as the front edge unit on the front edge of the arm section 512 is not particularly limited, and the imaging unit 515 may be configured as an endoscope or a microscope, for example. Additionally, the imaging unit 515 may also be configured to be removable from the arm section 512. According to such a configuration, an imaging unit 515 depending on the usage scenario may be connected appropriately to the front edge of the arm section 512 as the front edge unit, for example. Note that although the description herein focuses on a case in which the imaging unit 515 is applied as the front edge unit, obviously the front edge unit connected to the front edge of the arm section 512 is not necessarily limited to the imaging unit 515.

Also, at a position facing the user 520, a display device 550 such as a monitor or a display is installed. An image of the operating site captured by the imaging unit 515 is displayed as an electronic image on the display screen of the display device 550. The user 520 performs various treatments while looking at an electronic image of the operating site displayed on the display screen of the display device 550.

In this way, in the medical field, the present embodiment proposes performing surgery while imaging the operating site with the surgical video microscope device 510

Particularly, the surgical video microscope device 510 according to an embodiment of the present disclosure (that is, a medical stereoscopic observation device) is configured to be able to acquire image data for displaying the imaging target as a three-dimensional image (3D image).

As a specific example, the surgical video microscope device 510 is provided with a stereo camera including two imaging section subsystems (for example, camera units) as the imaging unit 515, and thereby acquires, via each imaging section, images from multiple different viewpoints (in other words, viewpoint images).

Each of the multiple viewpoint images acquired by the imaging unit 515 is subjected to various types of image processing by an image processing device built into or externally attached to the surgical video microscope device 510, and then displayed on the display device 550 as a left-eye image and a right-eye image, respectively. Note that in this description, the right-eye image denotes a so-called parallax image having a set parallax for observing a viewpoint corresponding to the user's right eye, to enable the user to observe a 3D image. Similarly, the left-eye image denotes a parallax image having a set parallax for observing a viewpoint corresponding to the user's left eye.

Note that a variety of techniques have been proposed as a mechanism for enabling the user 520 to observe, as a 3D image, the images displayed on the display device 550 as the left-eye image and the right-eye image. As a specific example, there is a technique in which special-purpose eyeglasses are used to cause the left and right eyes to observe mutually different images (in other words, a left-eye image and a right-eye image). Also, in recent years, glasses-free 3D picture technology which enables the observation of a three-dimensional image without the use of special-purpose eyeglasses has also been proposed.

In addition, the circumstances in which a medical observation device as described above is used also includes cases in which various information should be checked, including images of an affected area. Under such circumstances, usage patterns such as displaying images respectively on multiple displays or displaying multiple images inside a display may also be anticipated. As a specific example, a case is anticipated in which an overall picture of the affected area is displayed on one display, while a magnified image of the affected area is displayed on another display. As another example, a case is also anticipated in which an image of the affected area is displayed on one display, while an image captured by another imaging device, such as a computed tomography (CT) image or a magnetic resonance imaging (MRI) image, is displayed on another display. For this reason, multiple display devices 550 may also be provided in some cases.

The above thus references FIG. 1 to describe, as an applied example of using a medical stereoscopic observation device according to an embodiment of the present disclosure, a an example of a case in which a surgical video microscope device equipped with an arm is used as the medical stereoscopic observation device.

[1.2. Exterior Appearance of Medical Stereoscopic Observation Device]

Figure 2:
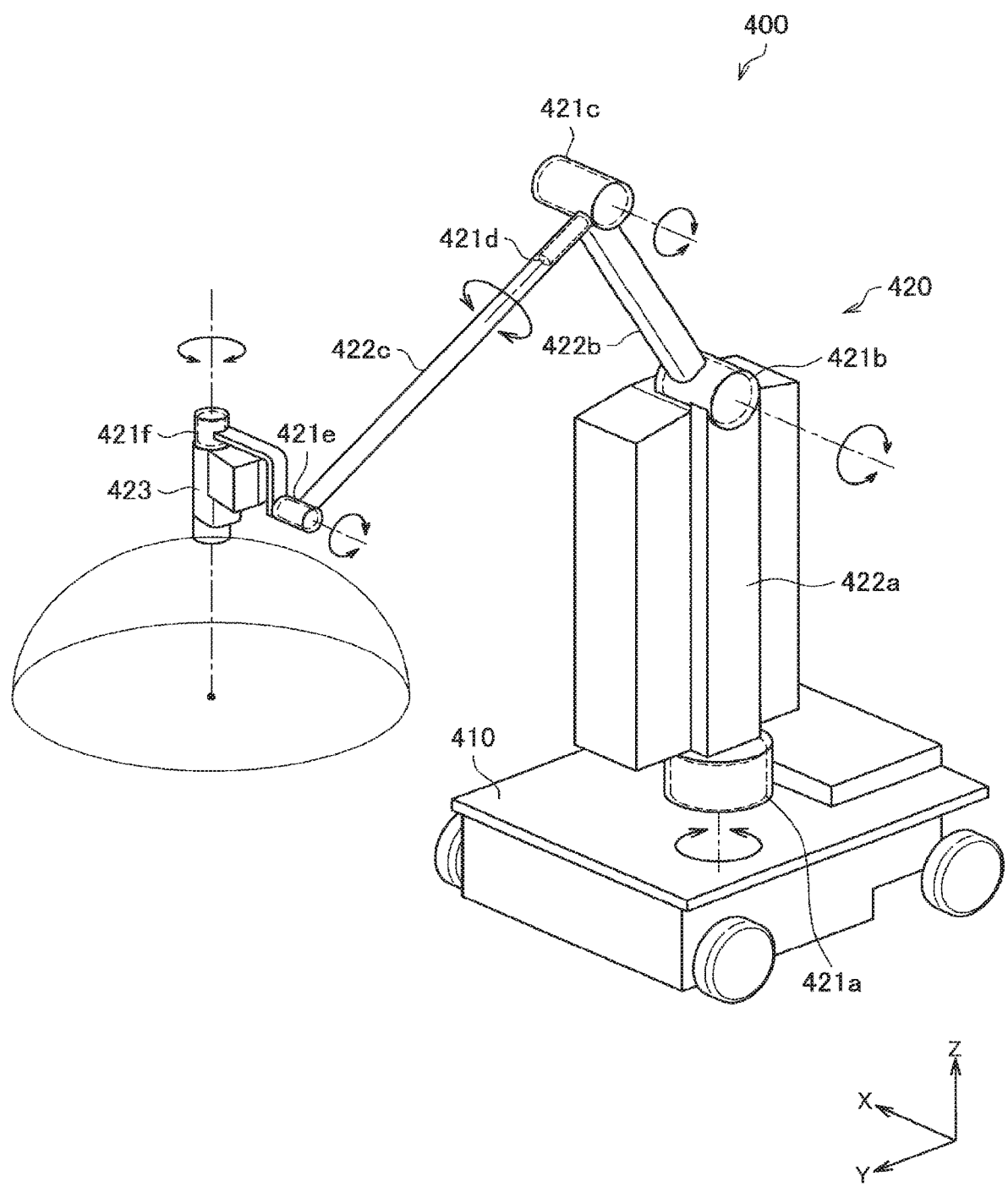
FIG. 2 is a schematic diagram illustrating an example of the exterior appearance of a medical stereoscopic observation device according to the embodiment.

Next, FIG. 2 will be referenced to describe a schematic configuration of a surgical video microscope device provided with an arm as an example of a surgical video microscope device (that is, a medical stereoscopic observation device) that acquires image data (that is, viewpoint images imaged from multiple viewpoints) for displaying an imaging target as a three-dimensional image, in a medical stereoscopic observation system according to an embodiment of the present disclosure. FIG. 2 is a schematic diagram illustrating an example of the exterior appearance of a medical stereoscopic observation device according to an embodiment of the present disclosure.

Referring to FIG. 2, an example of a medical stereoscopic observation device according to the present embodiment, namely, a surgical video microscope device 400, is provided with a base section 410 and an arm section 420. The base section 410 is the base of the surgical video microscope device 400, and the arm section 420 extends from the base section 410. Also, although not illustrated in FIG. 2, a control section that centrally controls the surgical video microscope device 400 may also be provided inside the base section 410, and the driving of the arm section 420 may be controlled by the control section. The control section is made up of any of various types of signal processing circuits, such as a central processing unit (CPU) or a digital signal processor (DSP), for example.

The arm section 420 includes multiple joint sections 421a to 421f, multiple links 422a to 422c joined to each other by the joint sections 421a to 421f, and an imaging unit 423 provided on the front end of the arm section 420.

The links 422a to 422c are rod-shaped members, in which one end of the link 422a is joined to the base section 410 via the joint section 421a, while the other end of the link 422a is joined to one end of the link 422b via the joint section 421b, and additionally, the other end of the link 422b is joined to one end of the link 422c via the joint sections 421c and 421d. Additionally, the imaging unit 423 is joined to the front end of the arm section 420, or in other words the other end of the link 422c, via the joint sections 421e and 421f. In this way, the base section 410 acts as a fulcrum, and the ends of the multiple links 422a to 422c are joined to each other by the joint sections 421a to 421f, thereby constituting an arm shape extending from the base section 410.

The imaging unit 423 is a unit that acquires an image of an imaging target, and may be configured by a device such as a camera that captures a moving image or a still image, for example. By controlling the driving of the arm section 420, the position and attitude of the imaging unit 423 are controlled. In the present embodiment, the imaging unit 423 images a partial region of a patient's body, the partial region being an operating site, for example. Note that, as described above, in the surgical video microscope device 400 according to the present embodiment, the imaging unit 423 is configured to be able to acquire images from multiple different viewpoints (that is, image data for displaying the imaging target as a three-dimensional image), like a stereo camera, for example.

Herein, in the following, the surgical video microscope device 400 will be described by defining coordinate axes as illustrated in FIG. 2. Also, an up-and-down direction, a forward-and-back direction, and a right-and-left direction are defined to match the coordinate axes. Namely, the up-and-down direction with respect to the base section 410 installed on the floor is defined to be the z-axis direction and the up-and-down direction. Also, the direction which is orthogonal to the z-axis, and in which the arm section 420 extends from the base section 410 (in other words, the direction in which the imaging unit 423 is positioned with respect to the base section 410) is defined to be the y-axis direction and the forward-and-back direction. Additionally, the direction that is orthogonal to the y-axis and the z-axis is defined to be the x-axis direction and the left-and-right direction.

The joint sections 421a to 421f rotatably join the links 422a to 422c to each other. Each of the joint sections 421a to 421f includes an actuator, and includes a rotation mechanism that is rotationally driven about a certain rotation axis by the driving of the actuator. By respectively controlling the rotational driving in each of the joint sections 421a to 421f, driving of the arm section 420 can be controlled so as to extend or contract (fold up) the arm section 420, for example. Also, as described above, since the joint sections 421a to 421f include a rotating mechanism, in the following description, driving control of the joint sections 421a to 421f specifically means that the rotational angle and/or the generated torque of the joint sections 421a to 421f (the torque generated by the joint sections 421a to 421f) are controlled.

In the example of the surgical video microscope device 400 illustrated in FIG. 2, six joint sections 421a to 421f are included, and six degrees of freedom are realized with respect to the driving of the arm section 420. Specifically, as illustrated in FIG. 2, the joint sections 421a, 421d, and 421f are provided to take the longitudinal directions of each of the connected links 422a to 422c as well as the imaging direction of the connected imaging unit 423 as rotation axis directions, while the joint sections 421b, 421c, and 421e are provided to take the x-axis direction as a rotation axis direction, the x-axis direction being the direction about which the joining angles of the respectively connected links 422a to 422c as well as the imaging unit 423 are changed in the y-z plane (the plane defined by the y-axis and the z-axis). In this way, in the present embodiment, the joint sections 421a, 421d, and 421f have a function of performing what is called yawing, while the joint sections 421b, 421c, and 421e have a function of performing what is called pitching.

By having such a configuration of the arm section 420, six degrees of freedom are realized with respect to the driving of the arm section 420 in the surgical video microscope device 400 according to the present embodiment, and thus the imaging unit 423 can be moved freely within the movable range of the arm section 420. In FIG. 2, a hemisphere is illustrated as one example of the movable range of the imaging unit 423. Provided that the hemisphere center point is the imaging center of the operating site imaged by the imaging unit 423, by causing the imaging unit 423 to move over the hemispherical surface of the hemisphere in a state in which the imaging center of the imaging unit 423 is locked to the hemisphere center point, the operating site can be imaged from a variety of angles.

Viewpoint images imaged from each of multiple viewpoints by the imaging unit 423 are transmitted to an image processing device (not illustrated) as a picture signal. Note that, as described above, the image processing device may be built into the surgical video microscope device 400, or may be externally attached to the surgical video microscope device 400 as an external device.

As a specific example, the image processing device may be built into the surgical video microscope device 400 by being provided inside the base section 410 of the surgical video microscope device 400. In this case, each viewpoint image imaged by the imaging unit 423 is transmitted inside the arm section 420 to the image processing device provided inside the base section 410, via a cable provided along the arm section 420. Subsequently, the image processing device performs various image processing on each transmitted viewpoint image, and then causes a display device to display the viewpoint images as a left-eye image and a right-eye image.

The above thus references FIG. 2 to describe a schematic configuration of a surgical video microscope device provided with an arm as an example of a surgical video microscope device that acquires viewpoint images for displaying an imaging target as a three-dimensional image, in a medical stereoscopic observation system according to the present embodiment.

[1.3. Schematic Functional Configuration of Medical Stereoscopic Observation System]

Figure 3:
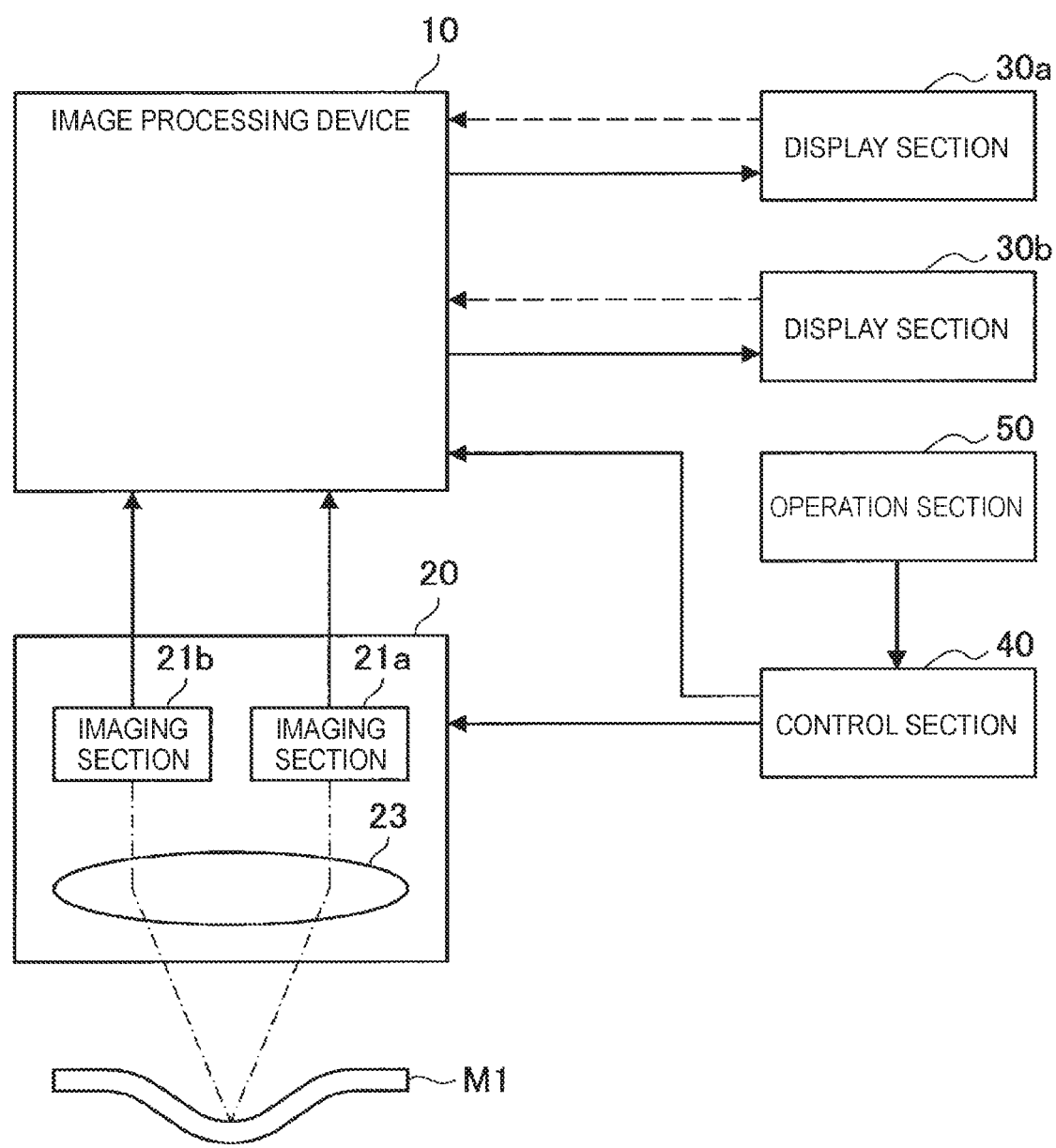
FIG. 3 is a block diagram illustrating an example of a schematic functional configuration of a medical stereoscopic observation system according to the embodiment.

Next, FIG. 3 will be referenced to describe an example of a schematic functional configuration of a medical stereoscopic observation system according to the present embodiment, with particular focus on a process of outputting a left-eye image and a right-eye image on the basis of viewpoint images imaged by an imaging unit from each of multiple viewpoints. FIG. 3 is a block diagram illustrating an example of a schematic functional configuration of a medical stereoscopic observation system according to the present embodiment, and illustrates an example of a functional configuration with particular focus on operations by which an image processing device acquires respective viewpoint images, and outputs a left-eye image and a right-eye image on the basis of the viewpoint images.

As illustrated in FIG. 3, the medical stereoscopic observation system according to the present embodiment includes an imaging unit 20, an image processing device 10, display sections 30a and 30b, a control section 40, and an operation section 50. Note that each of the display sections 30a and 30b corresponds to an example of the display device 550 described above with reference to FIG. 1. Note that in the following description, the display sections 30a and 30b may be designated simply the "display section 30" when not being particularly distinguished.

The imaging unit 20 is a configuration for acquiring respective viewpoint images by imaging an observation target M1 from multiple viewpoints. As illustrated in FIG. 3, the imaging unit 20 includes imaging sections 21a and 21b, and an optical system 23, for example.

The imaging sections 21a and 21b may include an image sensor such as a complementary metal-oxide semiconductor (CMOS) image sensor or a charge-coupled device (CCD) image sensor, for example. Note that in the following description, the imaging sections 21a and 21b may be designated simply the "imaging section 21" when not being particularly distinguished. Also, the optical system 23 includes lenses and the like, and is a configuration for forming an image of the imaging target onto the image sensor of the imaging section 21.

The imaging sections 21a and 21b respectively image the imaging target from respectively different viewpoints, and output each of the imaged viewpoint images to the image processing device 10 positioned downstream. The imaging sections 21a and 21b may also be configured to be able to capture moving images. Note that the respective viewpoint images imaged by the imaging sections 21a and 21b and output from the imaging sections 21a and 21b to the image processing device 10 correspond to an example of "input image data".

The control section 40 is a configuration for controlling the operations of the imaging unit 20 and the image processing device 10.

As a specific example, the control section 40 may control the operations of the imaging unit 20 to thereby adjust the distance between the imaging unit 20 and the observation target M1 (hereinafter designated the "working distance" in some cases), or adjust the position of the optical system 23 to thereby control the magnification of optical zoom.

Also, as another example, the control section 40 may control the operations of the image processing device 10 to thereby control the magnification of what is called electronic zoom that magnifies a portion of each imaged viewpoint image, or to control the types of image processing, and various parameters of such image processing, performed on the imaged viewpoint images.

Note that the control section 40 may also execute the various controls described above on the basis of instructions from the user via the operation section 50, for example. The operation section 50 corresponds to an input device by which the user operates the various components of the medical stereoscopic observation system according to the present embodiment.

Also, as another example, the control section 40 may also execute the various controls described above on the basis of sensing results from various sensing sections, such as a range sensor or an optical sensor. As a specific example, the control section 40 may control the position of the imaging unit 20 so that the working distance becomes a certain value, on the basis of a sensing result of the distance between the imaging unit 20 and the observation target M1 from what is called a range sensor.

The image processing device 10 acquires an imaged viewpoint image from each of the imaging sections 21a and 21b, and performs various image processing on these viewpoint images. In addition, the image processing device 10 may also generate a magnified image of each viewpoint image by electronically cropping a portion of the imaged viewpoint images with what is called electronic zoom.

Additionally, the image processing device 10 computes a parallax value between the right-eye image and the left-eye image for causing the user to observe a three-dimensional image, in accordance with parameters related to an imaging state by which the imaging sections 21a and 21b image the viewpoint images, and parameters related to a viewing state by which the user views an image via the display section 30.

Note that examples of parameters related to the imaging state include, for example, the distance between the respective optical axes of the imaging sections 21a and 21b, and the distance between the imaging unit 20 and the observation target M1 (in other words, the working distance). Also, examples of parameters related to the viewing state include, for example, the distance between the display section 30 and the user (also known as the viewing distance). Additionally, preset values may also be set for the parameters related to the imaging state and the parameters related to the viewing state, in accordance with an anticipated usage scenario. Also, as another example, the parameters related to the imaging state and the parameters related to the viewing state may be updated dynamically in accordance with a detection result of each state by a sensing section, such as various sensors or the like.

Subsequently, the image processing device 10 adjusts the parallax of the viewpoint images subjected to image processing on the basis of the computed parallax value to thereby generate a right-eye image and a left-eye image, and outputs the generated right-eye image and left-eye image to the display section 30. On the basis of such a configuration, when each of the right-eye image and the left-eye image displayed on the display section 30 is observed by the corresponding eye of the user, the user becomes able to observe a three-dimensional image based on the right-eye image and the left-eye image.

The above thus references FIG. 3 to describe an example of a schematic functional configuration of a medical stereoscopic observation system according to the present embodiment, with particular focus on a process that outputs a left-eye image and a right-eye image on the basis of viewpoint images imaged by an imaging unit from each of multiple viewpoints. Note that the functional configuration of a medical stereoscopic observation system according to the present embodiment illustrated in FIG. 3 is merely one example, and the configuration is not necessarily limited to the example illustrated in FIG. 3, insofar as the various operations described above are realizable. As a specific example, at least a portion of the components of the medical stereoscopic observation system illustrated in FIG. 3 may also be provided inside the same housing.

2. Investigation of Medical Stereoscopic Observation Device

Next, to more easily understand the features of a medical stereoscopic observation device according the present embodiment, an example of a mechanism for causing a user to observe a three-dimensional image will be described first, followed by a summary of the challenges of such a medical stereoscopic observation device.

In a stereoscopic observation device that displays an image to be presented as a stereoscopic three-dimensional image, by causing a display section to display a right-eye image and a left-eye image with a set parallax, and by causing a user to observe each of the images from a corresponding viewpoint (that is, with the right eye or the left eye), the user is made to observe a three-dimensional image, for example. Note that, regarding a mechanism for causing each of a right-eye image and a left-eye image to be observed from a corresponding viewpoint, long-standing methods using specialized glasses have been proposed. Meanwhile, in recent years, glasses-free 3D picture technology has also been proposed, in which an optical member such as a lenticular panel or parallax barrier is used to form each of a right-eye image and a left-eye image displayed on a display section from a corresponding viewpoint, thereby enabling a user to observe a three-dimensional image without the use of specialized glasses. Note that, regarding a detailed mechanism for causing each of a right-eye image and a left-eye image to be observed from a corresponding viewpoint as indicated above, since the content is generally known, a detailed description is omitted from the description herein.

Figure 4:
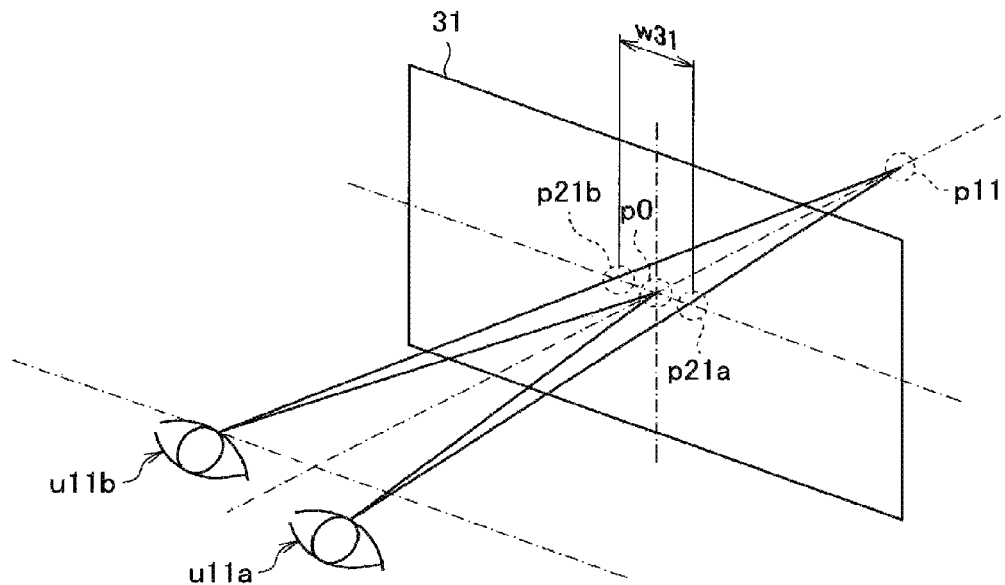
FIG. 4 is an explanatory diagram for explaining an example of a mechanism for causing a user to observe a three-dimensional image.
Figure 5:
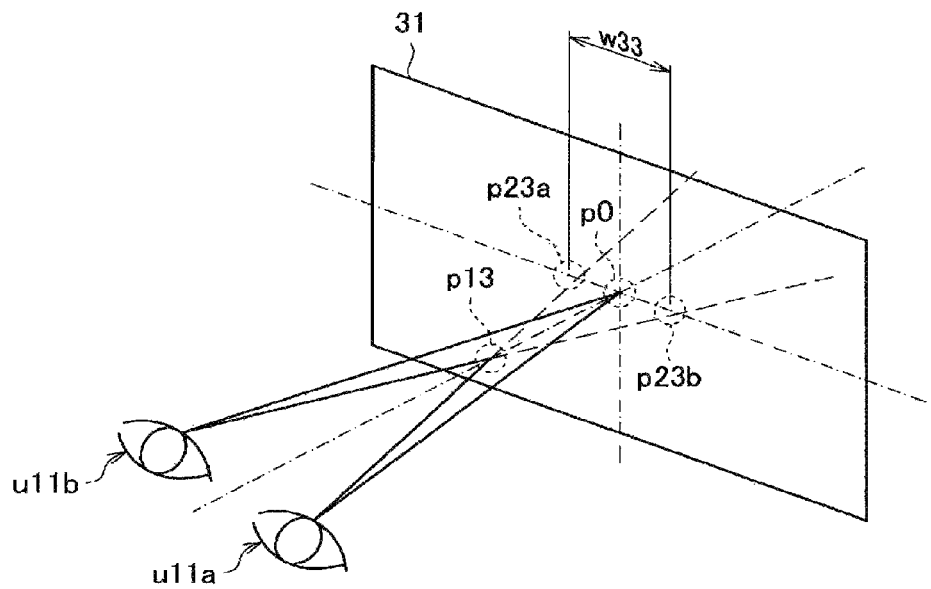
FIG. 5 is an explanatory diagram for explaining an example of a mechanism for causing a user to observe a three-dimensional image.

Herein, FIGS. 4 and 5 will be referenced to describe an overview of a control method of controlling a position in the depth direction of an image to be presented, in the case of causing a user to observe a three-dimensional image. FIGS. 4 and 5 are explanatory diagrams for explaining an example of a mechanism for causing a user to observe a three-dimensional image.

In FIGS. 4 and 5, the reference sign 31 schematically indicates a display screen on which the display section 30 displays an image. Also, the reference sign u11a schematically indicates the position of a viewpoint corresponding to the user's right eye. Similarly, the reference sign u11b schematically indicates the position of a viewpoint corresponding to the user's left eye. Note that the viewpoints u11a and u11b may be designated simply the "viewpoints u11" when not being particularly distinguished.

For example, FIG. 4 illustrates an example of a case of causing the user to observe an image to be presented at a position behind the display screen 31.

In FIG. 4, the reference sign p11 schematically indicates the image to be presented, which is observed by the user. Also, the reference sign p21a schematically indicates a right-eye image which corresponds to the image p11 and which is displayed on the display screen 31. Similarly, the reference sign p21b schematically indicates a left-eye image which corresponds to the image p11 and which is displayed on the display screen 31. Note that the series of images presented by the parallax images corresponding to each of the viewpoints (in other words, the right-eye image and the left-eye image) are hereinafter designated "multi-viewpoint images" in some cases.

Also, the reference sign p0 schematically indicates the display position of an image observed from both of the viewpoints u11a and u11b in the case in which the image to be presented is displayed so as to be positioned on the display screen 31. Note that in this case, the position where such an image is displayed corresponds to the position where the corresponding image is observed by the user.

Herein, the image p11 to be presented is observed by the user so as to be displayed at a position where the line-of-sight direction in the case of observing the right-eye image p21a from the viewpoint u11a corresponding to the right eye and the line-of-sight direction in the case of observing the left-eye image p21b from the viewpoint u11b corresponding to the left eye intersect.

In the example illustrated in FIG. 4, in a case in which the user views the display screen 31 straight on, the respective viewpoint images are displayed so that the right-eye image p21a is positioned on the right side with respect to the display position p0, while the left-eye image p21b is positioned on the left side with respect to the display position p0. In such a case, the line-of-sight direction in the case of observing the right-eye image p21a from the viewpoint u11a corresponding to the right eye and the line-of-sight direction in the case of observing the left-eye image p21b from the viewpoint u11b corresponding to the left eye intersect behind the display screen 31. In other words, in the example illustrated in FIG. 4, the image to be presented is observed by the user as an image p11 displayed behind the display screen 31.

Note that the reference sign w31 indicates the spacing between the display position p0 of an image in the case in which the image to be presented is positioned on the display screen 31, and each of the parallax images (for example, the right-eye image p21a and the left-eye image p21b). This spacing is decided in accordance with what is called the parallax value. Note that in the following description, the spacing in real space between the display position p0 and each of the parallax images displayed on the display screen 31 will be designated the "display spacing based on the parallax value", or simply the "display spacing" in some cases. In other words, in the example illustrated in FIG. 4, as the display spacing w31 based on the parallax value increases, the position in the depth direction at which the image p11 is observed becomes shifted farther behind the display screen 31.

Meanwhile, FIG. 5 illustrates an example of a case of causing the user to observe an image to be presented at a position in front of the display screen 31.

In FIG. 5, the reference sign p13 schematically indicates the image to be presented, which is observed by the user. Also, the reference sign p23a schematically indicates a right-eye image which corresponds to the image p13 and which is displayed on the display screen 31. Similarly, the reference sign p23b schematically indicates a left-eye image which corresponds to the image p11 and which is displayed on the display screen 31. Note that, similarly to the example illustrated in FIG. 4, the reference sign p0 schematically indicates the display position of an image observed from both of the viewpoints u11a and u11b in the case in which the image to be presented is displayed so as to be positioned on the display screen 31.

Herein, in the example illustrated in FIG. 5, in a case in which the user views the display screen 31 straight on, the respective parallax images are displayed so that the right-eye image p23a is positioned on the left side with respect to the display position p0, while the left-eye image p23b is positioned on the left side with respect to the display position p0. In such a case, the line-of-sight direction in the case of observing the right-eye image p21a from the viewpoint u11a corresponding to the right eye and the line-of-sight direction in the case of observing the left-eye image p21b from the viewpoint u11b corresponding to the left eye intersect in front of the display screen 31. In other words, in the example illustrated in FIG. 5, the image to be presented is observed by the user as an image p13 displayed in front of the display screen 31.

Note that the reference sign w33 indicates the spacing (that is, the display spacing based on the parallax value) between the display position p0 of an image in the case in which the image to be presented is positioned on the display screen 31, and each of the parallax images (for example, the right-eye image p23a and the left-eye image p23b). In other words, in the example illustrated in FIG. 5, as the display spacing w33 based on the parallax value increases, the position in the depth direction at which the image p13 is observed becomes shifted farther in front of the display screen 31.

Next, FIGS. 6 to 10 will be referenced to describe the relationship between the distance in the depth direction in real space, and the distance in the depth direction observed by the user. FIGS. 6 to 10 are explanatory diagrams for explaining an example of a mechanism for causing a user to observe a three-dimensional image.

Figure 6:
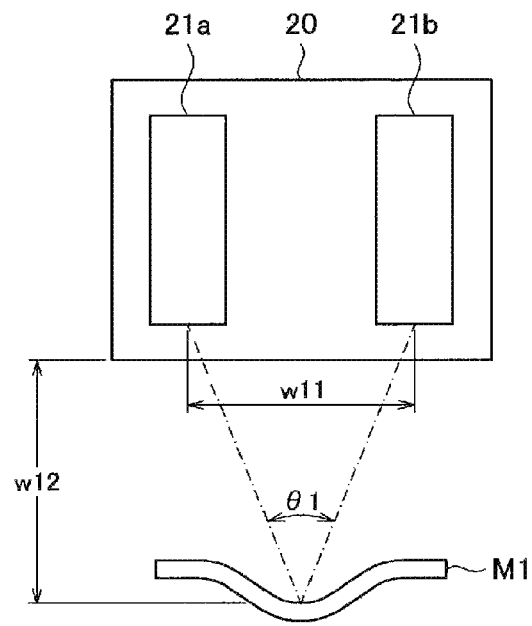
FIG. 6 is an explanatory diagram for explaining an example of a mechanism for causing a user to observe a three-dimensional image.

For example, FIG. 6 schematically illustrates the positional relationship between the observation target M1 and the imaging sections corresponding to each of the viewpoints (that is, the imaging sections 21a and 21b of the imaging unit 20), in the case of imaging an image of an observation target from multiple viewpoints.

In FIG. 6, the reference sign w11 indicates the distance between the respective optical axes of the imaging sections 21a and 21b corresponding to each of the viewpoints (hereinafter designated the "inter-optical-axis distance" in some cases). In other words, in the case of replacing the imaging sections 21a and 21b with the user's left and right eyes, the distance indicated by the reference sign w11 corresponds to the distance between the user's right eye and left eye. Also, the reference sign w12 indicates the distance between the imaging unit 20 (that is, the imaging sections 21a and 21b) and the observation target M1 (in other words, the working distance).

Note that in the example illustrated in FIG. 6, illustration of the optical system 23 has been omitted to make the explanation easier to understand. In other words, in the case of disposing the optical system 23 between the imaging sections 21a, 21b and the observation target M1, the optical path is modified by the optical system 23, and thus the distance between the imaging sections 21a, 21b and the observation target M1 may vary in accordance with the properties of the optical system 23. Given the above, the working distance w12 illustrated in FIG. 6 is taken to correspond to the distance between the imaging sections 21a, 21b and the observation target M1 in the case in which the optical path is not modified by the optical system 23.

Also, in FIG. 6, the reference sign $\theta 1$ indicates what is called the inward angle, which is formed between the observation target M1 and each of the imaging sections 21a and 21b corresponding to each viewpoint. Note that the inward angle $\theta 1$ can be computed on the basis of the inter-optical-axis distance w11 and the working distance w12.

Figure 7:
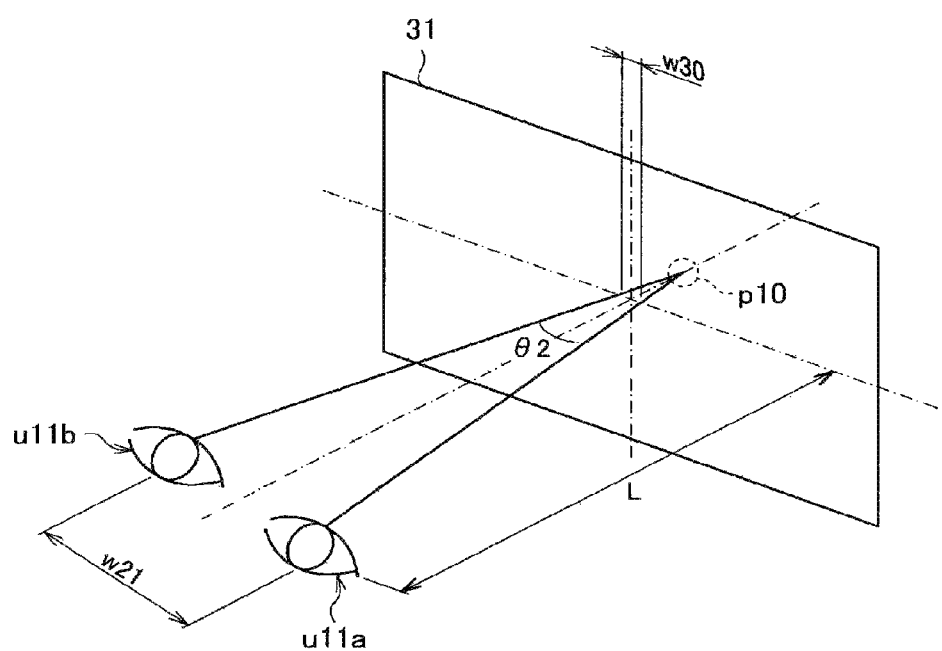
FIG. 7 is an explanatory diagram for explaining an example of a mechanism for causing a user to observe a three-dimensional image.

Next, FIG. 7 will be referenced. FIG. 7 schematically illustrates the positional relationship between the display screen 31 of the display section 30 and each viewpoint of the user (in other words, the viewpoint u11a corresponding to the right eye and the viewpoint u11b corresponding to the left eye), in the case in which the user observes a three-dimensional image displayed on the display section 30.

In FIG. 7, the reference sign w21 indicates the distance between the viewpoint u11a corresponding to the user's right eye and the viewpoint u11b corresponding to the left eye (hereinafter designated the "inter-viewpoint distance w21" in some cases). Also, the reference sign L indicates the distance between the user (that is, the viewpoints u11a and u11b) and the display screen 31 on which is displayed each of the viewpoint images for causing the user to observe a three-dimensional image (hereinafter designated the "viewing distance" in some cases). Also, the reference sign p10 schematically indicates the image observed by the user by displaying each of the viewpoint images (namely, the right-eye image and the left-eye image) being displayed on the display screen 31. Also, the reference sign w30 indicates the display spacing based on the parallax value for causing the user to observe the image p10.

Also, in FIG. 7, the reference sign $\theta 2$ illustrates what is called the angle of convergence, which is formed between the position of the image p10 to be observed by the user, and the positions of each of the viewpoints u11a and u11b Note that the angle of convergence $\theta 2$ can be computed on the basis of the inter-viewpoint distance w21, the viewing distance L, and the display spacing w30, for example. Note that the inter-viewpoint distance w21 and the viewing distance L may also be measured by any of various sensors, such as a range sensor or an optical sensor. Additionally, as another example, the inter-viewpoint distance w21 and the viewing distance L may also be preset in accordance with a viewing state which may be anticipated. For example, the inter-viewpoint distance w21 may be decided on the basis of a statistical value of the distance between the right eye and the left of the target users. Also, the viewing distance L may be decided in advance as a more favorable viewing state which may be anticipated, for example.

Herein, the ratio $\theta 1/\theta 2$ between the inward angle $\theta 1$ illustrated in FIG. 6 and the angle of convergence $\theta 2$ illustrated in FIG. 7 is taken to be the oblateness. At this point, as the oblateness $\theta 1/\theta 2$ approaches 1 (that is, as the difference between the inward angle $\theta 1$ and the angle of convergence $\theta 2$ becomes smaller), the user becomes able to observe the image p10 illustrated in FIG. 7 with a stereoscopic effect that is closer to the case of observing the observation target M1 with the imaging sections 21a and 21b acting as the right eye and the left eye in FIG. 6, respectively (in other words, a stereoscopic effect that is closer to the real thing).

Note that when displaying the respective viewpoint images on the display screen 31, if the display spacing w30 based on the parallax value is increased (that is, if the stereoscopic effect is strengthened), the distance in the depth direction between the display screen 31 and the image p10 becomes longer, the angle of convergence θ2 becomes smaller, and thus the oblateness θ1/θ2 becomes greater. In other words, if the oblateness θ1/θ2 is adjusted to be greater, the stereoscopic effect is strengthened more compared to the case of observing the observation target M1 with the imaging sections 21a and 21b acting as the right eye and the left eye, respectively.

Also, when displaying the respective viewpoint images on the display screen 31, if the display spacing w30 based on the parallax value is decreased (that is, if the stereoscopic effect is weakened), the distance in the depth direction between the display screen 31 and the image p10 becomes shorter, the angle of convergence θ2 becomes greater, and thus the oblateness θ1/θ2 becomes smaller. In other words, if the oblateness θ1/θ2 is adjusted to be smaller, the stereoscopic effect is weakened more compared to the case of observing the observation target M1 with the imaging sections 21a and 21b acting as the right eye and the left eye, respectively.

Note that prolonged viewing of three-dimensional images is known to induce eyestrain, and in particular, pronounced fatigue tends to be exhibited when viewing a picture having a large amount of parallax. For this reason, to reduce the sense of fatigue (namely, eyestrain) in the user viewing three-dimensional images, in some cases it is desirable to keep the parallax value contained within a certain range.

Specifically, the "parallax angle" is given as an example of a criterion for adjusting the parallax value. The parallax angle is expressed as the difference between the angle of convergence in the case of observing a position on the display screen 31 from the viewpoints u11a and u11b, and the angle of convergence in the case of observing the image to be presented from the viewpoints u11a and u11b. For example, FIGS. 8 and 9 are explanatory diagrams for explaining the parallax angle.

Figure 8:
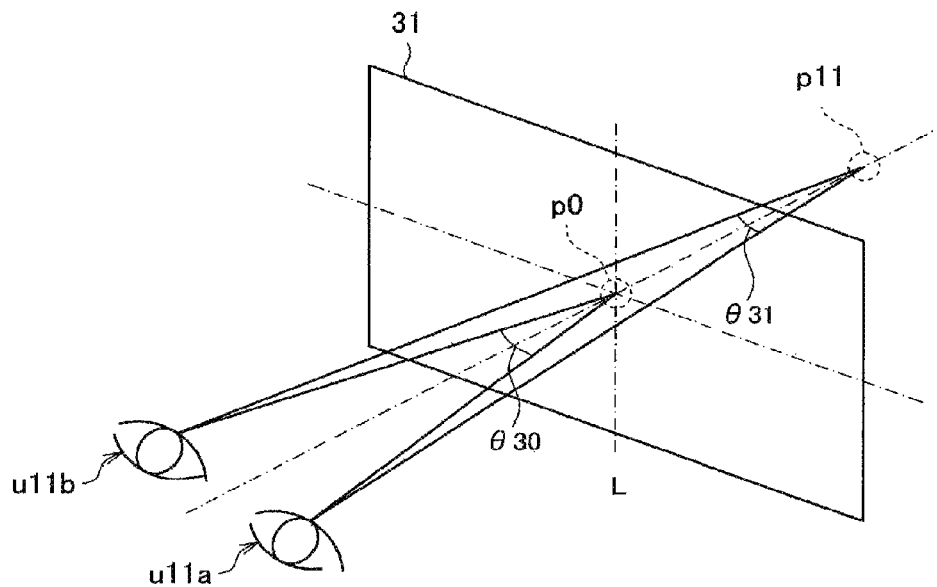
FIG. 8 is an explanatory diagram for explaining an example of a mechanism for causing a user to observe a three-dimensional image.

For example, FIG. 8 illustrates an example of a case of causing the user to observe the image p11 to be presented so that the image p11 is positioned behind the display screen 31. In the example illustrated in FIG. 8, the reference sign θ31 indicates the angle of convergence in the case of observing the image p11 from the viewpoints u11a and u11b. Also, the reference sign θ30 indicates the angle of convergence formed between the viewpoints u11a, u11b and a position on the display screen 31 (in other words, the angle of convergence in the case of displaying the image to be presented so that the image is positioned on the display screen 31). In other words, in the example illustrated in FIG. 8, the parallax angle is expressed as θ31-θ30.

Figure 9:
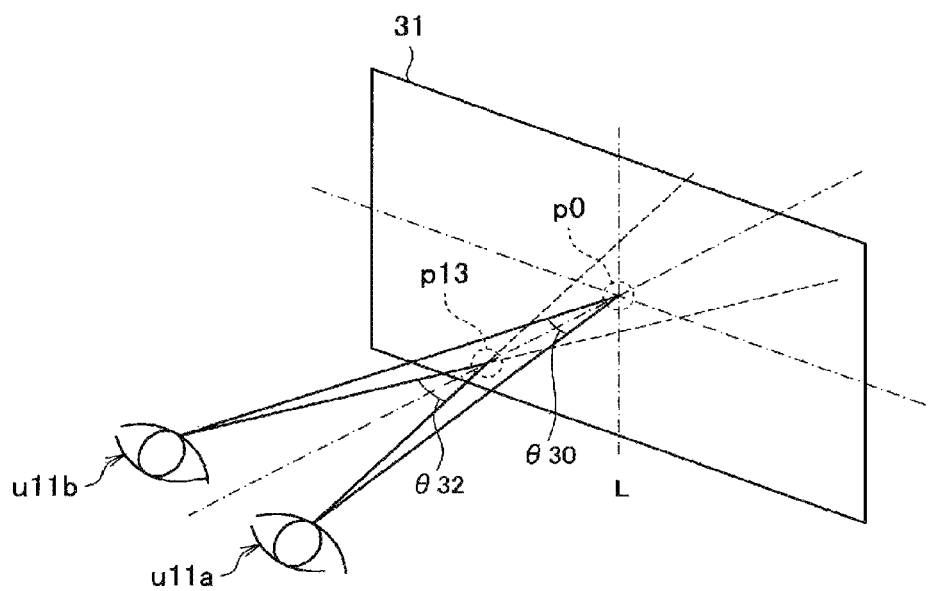
FIG. 9 is an explanatory diagram for explaining an example of a mechanism for causing a user to observe a three-dimensional image.

For example, FIG. 9 illustrates an example of a case of causing the user to observe the image p13 to be presented so that the image p13 is positioned in front of the display screen 31. In the example illustrated in FIG. 9, the reference sign θ32 indicates the angle of convergence in the case of observing the image p13 from the viewpoints u11a and u11b. Note that the reference sign θ30 is similar to the case of FIG. 8. In other words, in the example illustrated in FIG. 9, the parallax angle is expressed as θ30-θ32.

Generally, it is desirable to adjust the parallax value so that the parallax angle becomes one degree (60 arc minutes) or less. More specifically, the user is considered to be able to view three-dimensional images more comfortably (less likely to develop eyestrain) in the case in which the parallax angle is 35 arc minutes or less. Also, the user is considered to be able to view three-dimensional images without experiencing discomfort in the case in which the parallax angle is 40 arc minutes or less.

Figure 10:
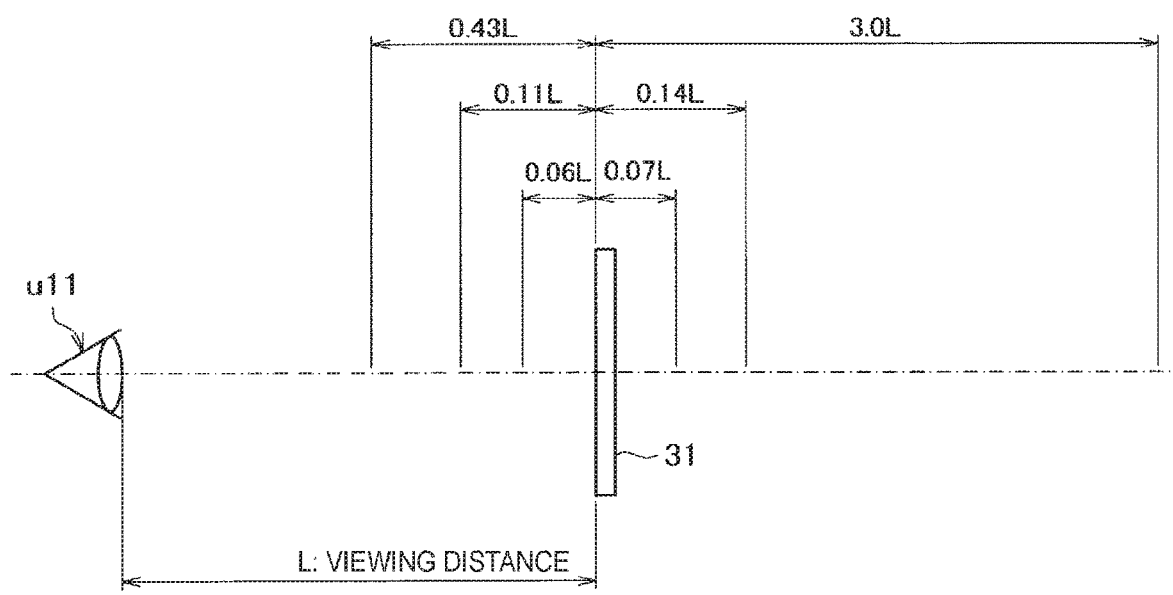
FIG. 10 is an explanatory diagram for explaining an example of a mechanism for causing a user to observe a three-dimensional image.

For example, FIG. 10 is an explanatory diagram for explaining a range of the parallax value over which the user is able to view three-dimensional images more easily (less likely to develop eyestrain). As illustrated in FIG. 10, provided that L is the viewing distance between a viewpoint u11 and the display screen 31, by adjusting the parallax value so that the distance in the depth direction between the position in the depth direction at which the image to be presented is observed and the display screen 31 becomes within 3.0 L behind and within 0.43 L in front, it is possible to adjust the parallax angle to be 60 arc minutes or less.

Also, by adjusting the parallax value so that the distance in the depth direction between the position in the depth direction at which the image to be presented is observed and the display screen 31 becomes within 0.14 L behind and within 0.11 L in front, it is possible to adjust the parallax angle to be 40 arc minutes or less. Similarly, by adjusting the parallax value so that the distance in the depth direction between the position in the depth direction at which the image to be presented is observed and the display screen 31 becomes within 0.06 L behind and within 0.07 L in front, it is possible to adjust the parallax angle to be 35 arc minutes or less.

On the other hand, in the case of causing the display section 30 to display what is called a multi-viewpoint image presented by a right-eye image and a left-eye image, the display spacing between the right-eye image and the left-eye image (in other words, the display spacing based on the parallax value) varies in accordance with the size (for example, the number of inches) and resolution (for example, the number of pixels) of the display section 30 in some cases.

Figure 11:
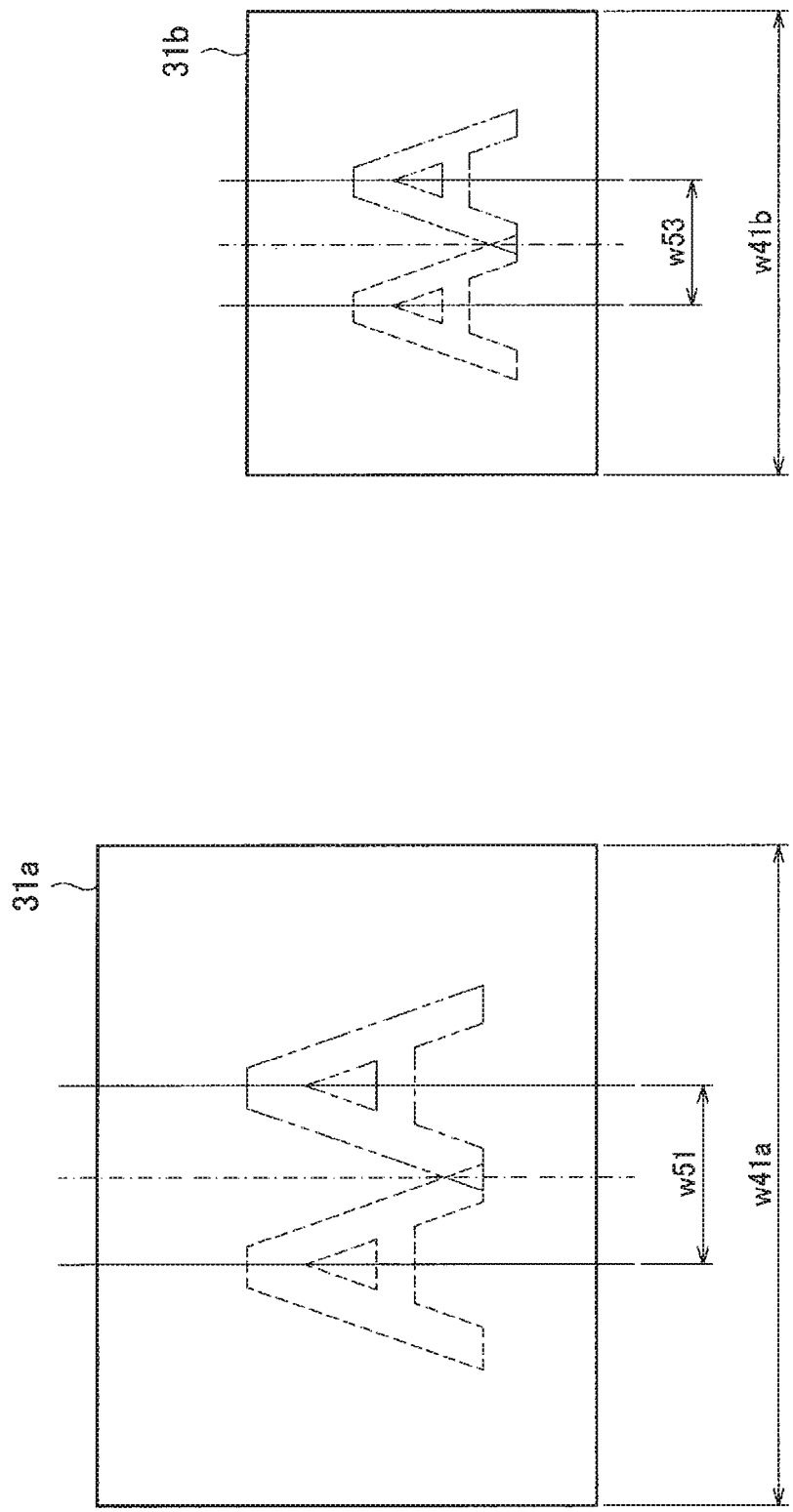
FIG. 11 is an explanatory diagram for explaining an overview of a medical stereoscopic observation system according to the embodiment.

For example, FIG. 11 is an explanatory diagram for explaining an overview of a medical stereoscopic observation system according to the present embodiment, and illustrates an example of a case of displaying a common multi-viewpoint image on display sections 30 of different sizes (for example, the number of inches).

In FIG. 11, the reference signs 31a and 31b schematically indicate the display screens 31 of the different display sections 30. Also, the reference sign w41a schematically indicates the horizontal width of the display screen 31a, or in other words, may correspond to the horizontal width of an image displayed on the display screen 31a. Similarly, the reference sign w41b schematically indicates the horizontal width of the display screen 31b, or in other words, may correspond to the horizontal width of an image displayed on the display screen 31b. At this time, the width w41a of the display screen 31a and the width w41b of the display screen 31b are taken to have the relationship w41a>w41b. In other words, the example illustrated in FIG. 11 illustrates an example of a case in which the display screen 31a is greater in size than the display screen 31b.

Also, in FIG. 11, the reference sign w51 indicates the display spacing based on the parallax value (in other words, the display spacing between the right-eye image and the left-eye image in real space) on the display screen 31a for causing the user to observe a three-dimensional image. Also, the reference sign w53 indicates the display spacing based on the parallax value (in other words, the display spacing between the right-eye image and the left-eye image in real space) on the display screen 31b for causing the user to observe a three-dimensional image.

Herein, in the case in which a common multi-viewpoint image is being displayed on both of the display screens 31a and 31b, the size difference between the display screen 31a and the display screen 31b causes the relationship between the display spacing w51 on the display screen 31a and the display spacing w53 on the display screen 31b to become w51>w53.

Herein, for the sake of simplicity, suppose that the display screens 31a and 31b both have the same resolution (number of pixels). In this case, the size (dimensions) in real space of one pixel on the larger-size screen 31a is greater than the size (dimensions) in real space of one pixel on the smaller-size display screen 31b. For this reason, even if the same parallax value (a value based on the number of pixels) is set for both the display screen 31a and the display screen 31b, the spacing in real space based on this parallax value (that is, the display spacing based on the parallax value) will be different between the display screen 31a and the display screen 31b. In other words, the display spacing w51 on the display screen 31a is wider than the display spacing w53 on the display screen 31b.

Figure 12:
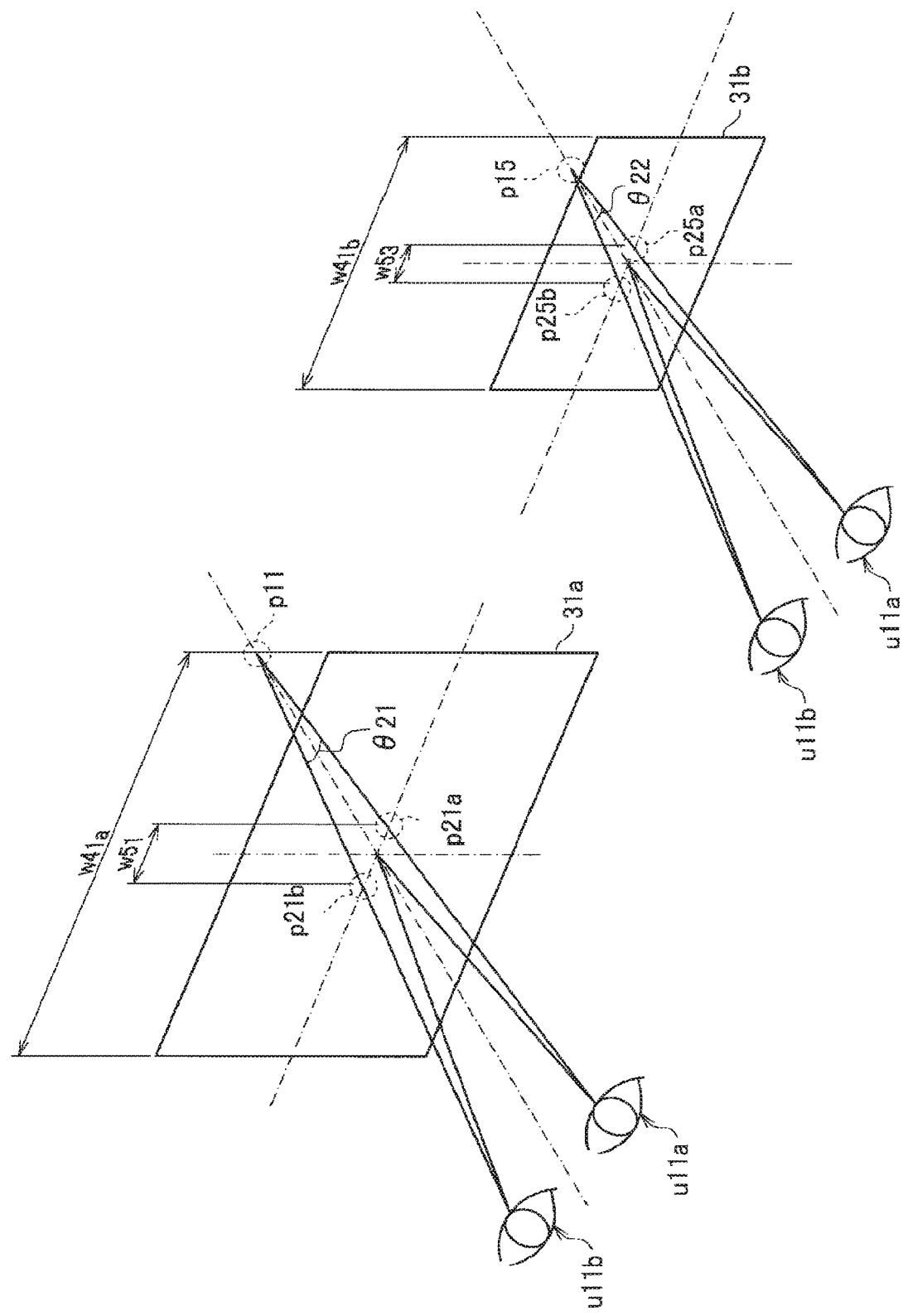
FIG. 12 is an explanatory diagram for explaining an overview of a medical stereoscopic observation system according to the embodiment.

The description will refer now to FIG. 12. FIG. 12 is an explanatory diagram for explaining an overview of a medical stereoscopic observation system according to the present embodiment. FIG. 12 illustrates an example of the display position in the depth direction of an image observed by a user in the case of observing a multi-viewpoint image displayed respectively on the display screens 31a and 31b illustrated in FIG. 11 at the same viewing distance. Note that in FIG. 12, parts which are similar to those illustrated in FIG. 11 are denoted with similar reference signs as in the case of FIG. 11.

Also, in FIG. 12, the reference signs p21a and p21b indicate the right-eye image and the left-eye image displayed on the display screen 31a. Also, the reference sign p11 indicates the image observed by the user due to the right-eye image p21a and the left-eye image p21b displayed on the display screen 31a. Similarly, the reference signs p25a and p25b indicate the right-eye image and the left-eye image displayed on the display screen 31b. Also, the reference sign p15 indicates the image observed by the user due to the right-eye image p25a and the left-eye image p25b displayed on the display screen 31b.

Also, the reference sign θ21 indicates the angle of convergence in the case of the user observing the image p11 due to the right-eye image p21a and the left-eye image p21b displayed on the display screen 31a. Similarly, the reference sign θ22 indicates the angle of convergence in the case of the user observing the image p15 due to the right-eye image p25a and the left-eye image p25b displayed on the display screen 31b.

As reference to FIG. 12 demonstrates, in the case of observing the multi-viewpoint image displayed on both of the display screens 31a and 31b at the same viewing distance, the difference between the display spacing w51 and the display spacing w53 causes the image p15 to be observed at a position farther in front than the image p11 (in other words, at a position closer to the display screen 31). Also, at this time, the relationship between the angle of convergence θ21 in the case of observing the image p11 and the angle of convergence θ22 in the case of observing the image p15 becomes θ21<θ22.

For this reason, between the case of observing the image p11 displayed on the display screen 31a and the case of observing the image p15 displayed on the display screen 31b of different size than the display screen 31a, the user observes the respective images with a different stereoscopic effect, even though the user is observing the same observation target. This is also clear from the difference between the oblateness θ1/θ21 in the case of observing the image p11 displayed on the display screen 31a, and the oblateness θ1/θ22 in the case of observing the image p15 displayed on the display screen 31a.

Note that although the above description focuses on the size (number of inches) of each display section 30, the display spacing based on the parallax value between the right-eye image and the left-eye image also varies due to the resolution (number of pixels) of the display section 30 in some cases.

For example, suppose that display sections 30c and 30d are display sections 30 having the same size (number of inches) but different resolution (number of pixels), and suppose that the resolution corresponding to the display section 30c is greater than the resolution corresponding to the display section 30d. At this time, the size (dimensions) in real space of one pixel on the display section 30c is smaller than the size (dimensions) in real space of one pixel on the display section 30d. For this reason, in the case of controlling the parallax value so that the display spacing based on the parallax value between the right-eye image and the left-eye image becomes approximately equal between the display sections 30c and 30d, the parallax value (a value based on the number of pixels) on the display section 30c side is controlled to become greater than the parallax value on the display section 30d side.

Particularly, in a medical stereoscopic observation system, a case may be anticipated in which the user performs a treatment on an observation target M1 (for example, an affected area) while confirming the observation target M1 on the basis of a three-dimensional image displayed on a display section. Under such circumstances, a situation in which the image of the observation target M1 is observed with a different stereoscopic effect on each of multiple display sections with different sizes is undesirable in some cases.

Accordingly, a medical stereoscopic observation system according to the present embodiment provides a mechanism enabling a user to observe a three-dimensional image in a more favorable mode on each of multiple display sections, regardless of differences in display conditions such as the size and resolution of each display section.

Figure 13:
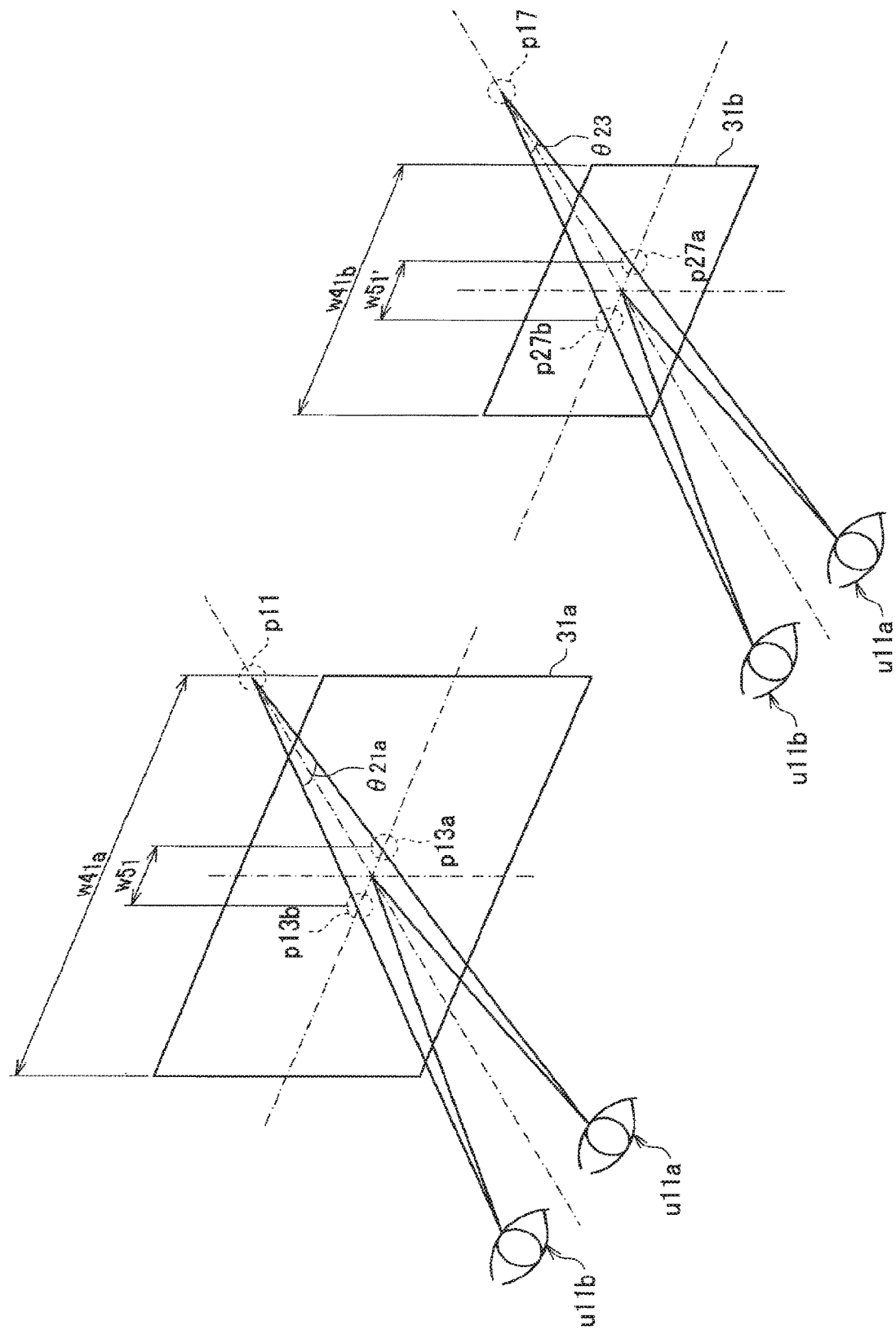
FIG. 13 is an explanatory diagram for explaining an overview of a medical stereoscopic observation system according to the embodiment.

For example, FIGS. 13 and 14 are explanatory diagrams for explaining an overview of a medical stereoscopic observation system according to the present embodiment, and illustrate an example of a method of presenting a three-dimensional image by such the medical stereoscopic observation system. Namely, in a case in which a user confirms an observation target M1 via each of display screens 31a and 31b of different size, FIGS. 13 and 14 illustrate an example of a mechanism for enabling three-dimensional images of the observation target M1 to be presented with a similar stereoscopic effect, regardless of the differences between the display screens.

In FIG. 13, the reference signs p27a and p27b indicate the right-eye image and the left-eye image displayed on the display screen 31b. Also, the reference sign p17 indicates the image observed by the user due to the right-eye image p27a and the left-eye image p27b displayed on the display screen 31b. Also, the reference sign w51' indicates the display spacing based on the parallax value (in other words, the display spacing between the right-eye image p27a and the left-eye image p27b in real space) on the display screen 31b. Also, the reference sign θ23 indicates the angle of convergence in the case of the user observing the image p17 due to the right-eye image p27a and the left-eye image p27b displayed on the display screen 31b.

In the example illustrated in FIG. 13, the display positions of the right-eye image p27a and the left-eye image p27b on the display screen 31b are controlled so that the relationship between the display spacing w51 on the display screen 31a and the display spacing w51' on the display screen 31b becomes w51=w51'. For example, FIG. 14 illustrates an example of a multi-viewpoint image (in other words, a right-eye image and a left-eye image) displayed on each of the display screens 31a and 31b.

By such control, in the example in FIG. 13, the distance in the depth direction between the display screen 31a and the image p11, and the distance in the depth direction between the display screen 31b and the image p17, become approximately equal. In other words, in the example illustrated in FIG. 13, the angle of convergence θ21 in the case of referencing the display screen 31a side, and the angle of convergence θ23 in the case of referencing the display screen 31b side, become approximately equal.

With this arrangement, according to the medical stereoscopic observation system according to the present embodiment, it becomes possible to observe a three-dimensional image with a similar stereoscopic effect, even under circumstances in which a user observes the three-dimensional image via each of multiple display sections having different display conditions.

3. Functional Configuration of Image Processing Device

Figure 15:
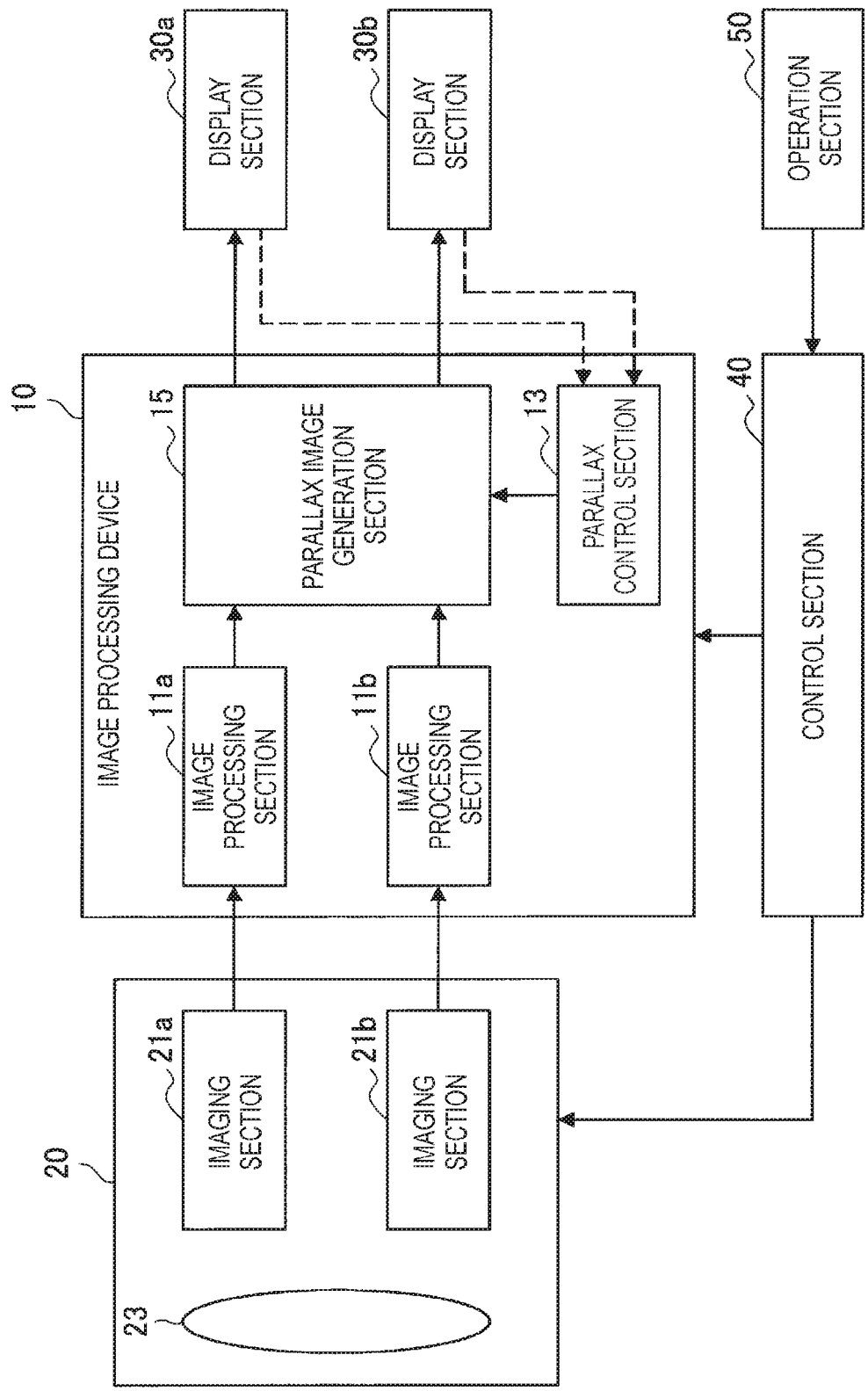
FIG. 15 is a block diagram illustrating an example of a functional configuration of an image processing device in a medical stereoscopic observation system according to the embodiment.

Next, an example of a detailed functional configuration of the image processing device 10 in the medical stereoscopic observation system according to the present embodiment illustrated in FIG. 3 will be described with reference to FIG. 15. FIG. 15 is a block diagram illustrating an example of a functional configuration of the image processing device 10 in the medical stereoscopic observation system according to the present embodiment. Note the following description will focus on the functional configuration of the image processing device 10. Other parts of the configuration have been described already, and thus detailed description of such parts will be reduced or omitted. Also, in the following description, the display sections 30a and 30b are taken to be provided as the multiple display sections 30, similarly to FIG. 3.

As illustrated in FIG. 15, the image processing device 10 according to the present embodiment includes image processing sections 11a and 11b, a parallax control section 13, and a parallax image generation section 15.

The image processing section 11a is a configuration for acquiring a viewpoint image imaged by the imaging section 21a as input image data, and performing various image processing on the input image data. Similarly, the image processing section 11b is a configuration for acquiring a viewpoint image imaged by the imaging section 21b, and performing various image processing on the viewpoint image. Note that in the following description, the image processing sections 11a and 11b may be designated simply the "image processing section 11" when not being particularly distinguished. Note that, For example, the image processing section 11 may perform image analysis on an acquired viewpoint image to thereby extract a target satisfying a specific configuration from the viewpoint image (such as a specific site or lesion, for example), and perform what is called a highlighting process to apply color to the extracted target. Also, as another example, the image processing section 11 may superimpose an image imaged by another imaging device, such as a CT or MRI, onto the acquired viewpoint image (fusion). Also, as another example, the image processing section 11 may form an image by extracting a special light component (a wavelength component having a certain band) from a viewpoint image imaged by utilizing special light, such as photofluorography. Additionally, the image processing section 11 may also perform a minimum level of image processing for displaying an acquired viewpoint image on the display section 30 as an electronic image. Note that the image processing described above is merely one example, and does not limit the content of the image processing that the image processing section 11 performs on a viewpoint image.

Note that the image processing section 11 may also switch the image processing to apply to the acquired viewpoint image on the basis of an instruction from the user, for example. In this case, the image processing section 11 may acquire, from the control section 40, control information indicating instruction control from the user via the operation section 50, and on the basis of the acquired control information, decide the image processing to apply to the viewpoint image. Additionally, the image processing that the image processing section 11 applies to the acquired viewpoint image may also be preset.

As above, the image processing section 11 performs image processing on an acquired viewpoint image, and outputs a viewpoint image that has been subjected to the image processing to the parallax image generation section 15.

The parallax control section 13 controls, for each display section 30, the parallax value for generating a multi-viewpoint image (that is, an image presented by a right-eye image and a left-eye image) to be displayed on each of the display sections 30a and 30b.

Specifically, the parallax control section 13 acquires control information indicating display conditions such as the size (number of inches) and the resolution (number of pixels) of each display section 30, and on the basis of the display conditions, computes the size in real space of a multi-viewpoint image displayed on each display section 30 (hereinafter designated the "display size" in some cases).

At this time, the parallax control section 13 may also acquire control information indicating the display conditions corresponding to a display section 30 from that display section 30. Note that this case obviously presupposes that the display section 30 is provided with a function for outputting information indicating the display conditions set for the display section 30 to the image processing device 10.

Also, as another example, the parallax control section 13 may also read out, from a certain storage area, control information indicating the display conditions corresponding to a display section 30, the control information being stored in advance in the storage area. Note that in this case, it is sufficient for the control section 40 to store control information indicating the display conditions of the display section 30 input by the user via the operation section 50 in the certain storage area, for example. Also, control information indicating the display conditions of each display section 30 may also be stored in advance in the certain storage area. In this case, it is sufficient for the parallax control section 13 to acquire identification information for identifying each display section 30 from the corresponding display section 30, and read out the control information corresponding to the acquired identification information from the certain storage area, for example. In addition, the parallax control section 13 may also directly acquire, from the control section 40, control information indicating the display conditions of the display section 30 input by the user via the operation section 50.

The parallax control section 13, on the basis of the display size computed for each display section 30, controls the parallax value between the right-eye image and the left-eye image to be displayed on the display section 30.

As a specific example, the parallax control section 13 controls (adjusts) the parallax value corresponding to each display section 30 so that the angle of convergence θ2 in the case of observing a three-dimensional image (in other words, a multi-viewpoint image) displayed on each display section 30 becomes approximately equal between the display sections 30a and 30b, as described with reference to FIGS. 13 and 14.

Additionally, the parallax control section 13 may also control the parallax value corresponding to each display section 30 so that the position in the depth direction of each image with respect to the display screen 31 observed on the basis of a multi-viewpoint image stays within a certain range based on the viewing distance L (for example, as illustrated in FIG. 10, within 3.0 L behind, and within 0.43 L in front). In other words, the parallax control section 13 may control the parallax value corresponding to each display section 30 so that the parallax angle stays within a certain range (for example, a parallax angle of one degree or less).

In this case, the parallax control section 13 may also use information set in advance as a viewing distance which may be anticipated for each display section 30 as control information indicating the viewing distance L. Also, as another example, the parallax control section 13 may use information indicating a distance between the display section 30 and the user measured by a range sensor or the like, for example, as control information indicating the viewing distance L.

In addition, to compute the parallax value corresponding to each display section 30, the parallax control section 13 may use information about the inward angle θ1 when each of the imaging sections 21a and 21b of the imaging unit 20 images an image of the observation target M1 (that is, each viewpoint image). In this case, for example, it is sufficient for the parallax control section 13 to compute the inward angle θ1 on the basis of the inter-optical-axis distance w11 of the imaging unit 20, and the working distance w12 when each of the imaging sections 21a and 21b of the imaging unit 20 image an image of the observation target M1. Also, at this point, it is sufficient for the parallax control section 13 to acquire information indicating set values of the working distance w12 and the inter-optical-axis distance w11 as a control result of the imaging unit 20 from an agent of control over the imaging unit 20, such as the control section 40, for example. Obviously, the parallax control section 13 may also acquire information indicating the set values of the working distance w12 and the inter-optical-axis distance w11 from the imaging unit 20.

In addition, in a case in which the imaging conditions when the imaging unit 20 images an image of the observation target M1 (namely, the working distance w12 and the inter-optical-axis distance w11) are predetermined, the parallax control section 13 may use information that has been preset as the working distance w12 and the inter-optical-axis distance w11.

Note that in the case of using information about the inward angle θ1, for each display section 30, the parallax control section 13 may control the parallax value corresponding to each display section 30 so that the oblateness θ1/θ2 based on the inward angle θ1 and the angle of convergence θ2 becomes a value close to 1 (that is, so that the angle of convergence θ2 becomes approximately equal to the inward angle θ1), for example.

Additionally, the parallax control section 13 may also control the parallax value corresponding to each display section 30 dynamically, in accordance with changes in the viewing state and the imaging state. For example, in the case of detecting a change in the viewing distance L (in other words, a change in the parallax angle) on the basis of a measurement result from a range sensor or the like, the parallax control section 13 may update the parallax value corresponding to each display section 30 on the basis of the changed viewing distance L (or parallax angle). Also, as another example, in the case in which the set value of at least one of the working distance w12 and the inter-optical-axis distance w11 changes as a result of the control of the imaging unit 20 by the control section 40, the parallax control section 13 may update the parallax value corresponding to each display section 30 on the basis of the changed set value.

Note that in the case in which the display conditions of the display section 30 being used or the settings being used as the viewing state (for example, the viewing distance L) and the imaging state (for example, the working distance w12 and the inter-optical-axis distance w11) are predetermined, a parallax value corresponding to such display conditions or such settings may be computed in advance as a preset. Note that multiple presets may also be computed in advance in accordance with differences in the viewing state and the imaging state as presets of the parallax value, for example. In this case, for example, the parallax control section 13 may switch the preset to use appropriately in accordance with the setting of the viewing state and the imaging state.

As above, for each display section 30, the parallax control section 13 computes the display size of a multi-viewpoint image displayed on the that display section 30, and on the basis of the computed display size, controls the parallax value corresponding to that display section 30. Subsequently, for each display section 30, the parallax control section 13 outputs information indicating the parallax value control result to the parallax image generation section 15.

The parallax image generation section 15 acquires, from the image processing section 11a, a viewpoint image that has been imaged by the imaging section 21a and subjected to image processing by the image processing section 11a. Similarly, the parallax image generation section 15 acquires, from the image processing section 11b, a viewpoint image that has been imaged by the imaging section 21b and subjected to image processing by the image processing section 11b. Also, for each display section 30, the parallax image generation section 15 acquires information indicating the parallax value control result (that is, the parallax value controlled on the basis of the display conditions of that display section 30) from the parallax control section 13.

The parallax image generation section 15 generates parallax images (that is, a right-eye image and a left-eye image) corresponding to each viewpoint of the user, on the basis of the viewpoint images corresponding to each of the viewpoints acquired from the image processing sections 11a and 11b, respectively, and the parallax value control result acquired for each display section 30. Subsequently, the parallax image generation section 15 generates what is called a multi-viewpoint image presented by the viewpoint images corresponding to each of the multiple viewpoints generated for each of the display section 30, on the basis of the parallax value control result, and causes the display section 30 to display the generated multi-viewpoint image.

Note that the respective parallax images presented in the multi-viewpoint image (that is, the right-eye image and the left-eye image) are separated by an optical member such as a lenticular sheet or a parallax barrier provided on the display section 30, for example, and the respective parallax images are observed from the corresponding viewpoints of the user (that is, the right eye and the left eye). With this arrangement, the user becomes able to observe a three-dimensional image via that display section 30.

Also, as described earlier with reference to FIGS. 13 and 14, in the medical stereoscopic observation system according to the present embodiment, the image processing device 10 adjusts the parallax value on the basis of the display conditions (that is, the size and resolution) of each display section 30, in accordance with the display size of an image (for example, a multi-viewpoint image) displayed on that display section 30. With this arrangement, even under circumstances in which a user observes a three-dimensional image of the observation target M1 via each of multiple display sections 30 having different display conditions, the user becomes able to observe the observation target M1 with a similar stereoscopic effect, regardless of the differences in the display conditions.

The above thus references FIG. 15 to describe an example of a detailed functional configuration of the image processing device 10 in the medical stereoscopic observation system according to the present embodiment illustrated in FIG. 3. Note that the functional configuration of the image processing device 10 illustrated in FIG. 15 is merely one example, and is not necessarily limited to the example illustrated in FIG. 15, insofar as the various operations described above are realizable. As a specific example, at least a portion of the components of the image processing device 10 illustrated in FIG. 15 may also be provided in an external device different from the image processing device 10 (for example, the imaging unit 20, the display section 30, or another external device).

4. Flow of Processes by Image Processing Device

Figure 16:
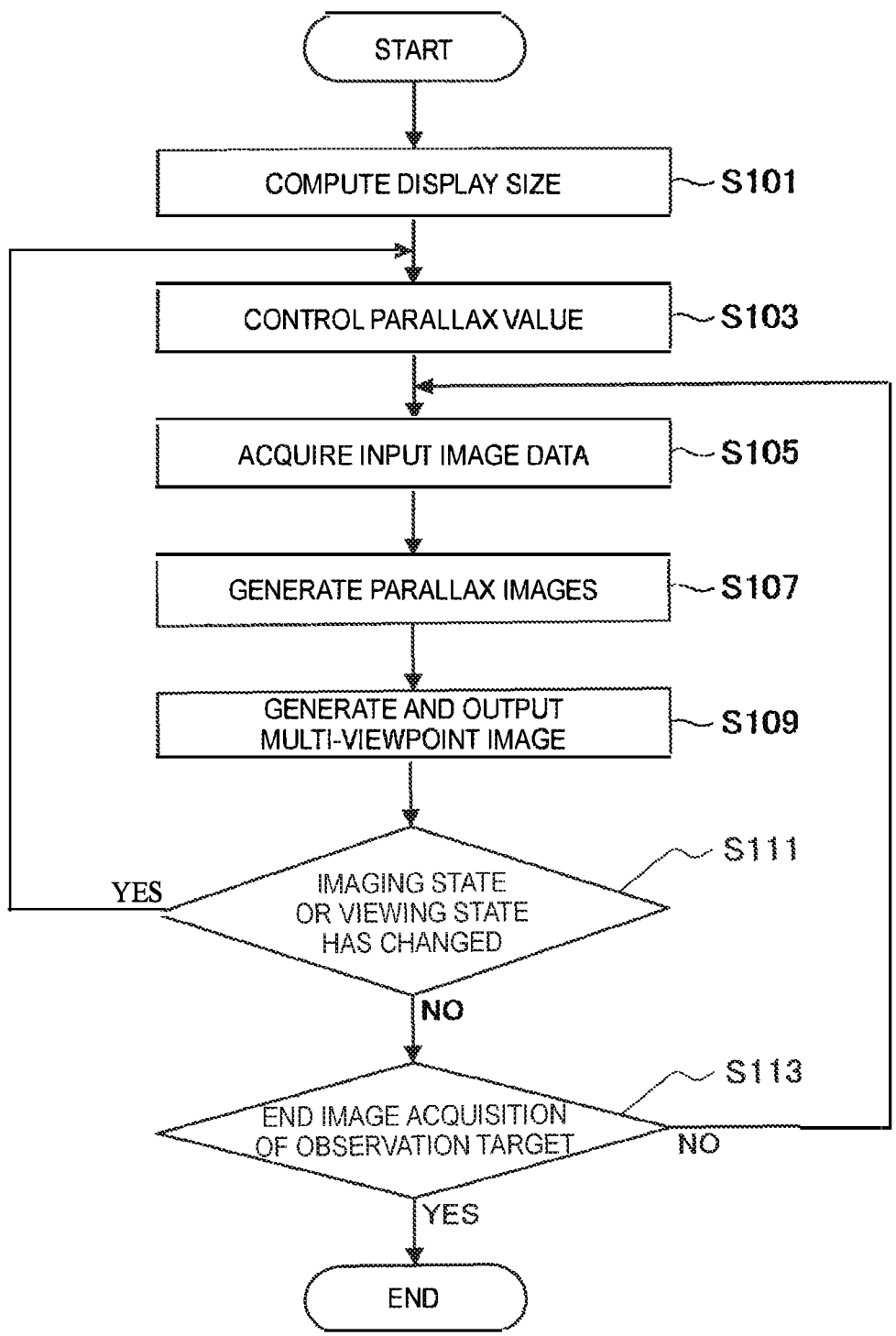
FIG. 16 is a flowchart illustrating an example of the flow of a series of operations by a medical stereoscopic observation system according to the embodiment.

Next, FIG. 16 will be referenced to describe an example of the flow of a series of operations by the medical stereoscopic observation system according to the present embodiment, with particular focus on operations by the image processing device 10. FIG. 16 is a flowchart illustrating an example of the flow of a series of operations by the medical stereoscopic observation system according to the present embodiment.

(Step S101)

The parallax control section 13 acquires control information indicating display conditions such as the size (number of inches) and the resolution (number of pixels) of each display section 30, and on the basis of the display conditions, computes the display size of a multi-viewpoint image displayed on each display section 30. At this time, the parallax control section 13 may also acquire control information indicating the display conditions corresponding to a display section 30 from that display section 30. Also, as another example, the parallax control section 13 may also read out, from a certain storage area, control information indicating the display conditions corresponding to a display section 30, the control information being stored in advance in the storage area.

(Step S103)

Next, the parallax control section 13, on the basis of the display size computed for each display section 30, controls the parallax value between the right-eye image and the left-eye image to be displayed on the display section 30.

At this time, the parallax control section 13 may also control the parallax value corresponding to each display section 30 so that the angle of convergence θ2 in the case of observing a three-dimensional image (in other words, a multi-viewpoint image) displayed on each display section 30 becomes approximately equal among the multiple display sections 30, for example. Note that at this time, the parallax control section 13 may also compute the parallax value corresponding to each display section 30 in accordance with a detection result of a viewing state (for example, the viewing distance L) by which the user views an image via each display section 30.

Also, as another example, the parallax control section 13 may control the parallax value corresponding to each display section 30 so that the position in the depth direction of each image with respect to the display screen 31 observed on the basis of a multi-viewpoint image stays within a certain range.

In addition, to compute the parallax value corresponding to each display section 30, the parallax control section 13 may use information about the inward angle θ1 when each of the imaging sections 21a and 21b of the imaging unit 20 images an image of the observation target M1 (that is, each viewpoint image). In this case, for example, it is sufficient for the parallax control section 13 to compute the inward angle θ1 on the basis of the inter-optical-axis distance w11 of the imaging unit 20, and the working distance w12 when the imaging unit 20 images an image of the observation target M1.

As above, for each display section 30, the parallax control section 13 computes the display size of a multi-viewpoint image displayed on the that display section 30, and on the basis of the computed display size, controls the parallax value corresponding to that display section 30. Subsequently, for each display section 30, the parallax control section 13 outputs information indicating the parallax value control result to the parallax image generation section 15.

(Step S105)

The image processing section 11a acquires a viewpoint image imaged by the imaging section 21a as input image data, performs various image processing on the input image data, and outputs the viewpoint image subjected to image processing to the parallax image generation section 15. Similarly, the image processing section 11b acquires a viewpoint image imaged by the imaging section 21b as input image data, performs various image processing on the input image data, and outputs the viewpoint image subjected to image processing to the parallax image generation section 15.

The parallax image generation section 15 acquires, from the image processing section 11a, a viewpoint image that has been imaged by the imaging section 21a and subjected to image processing by the image processing section 11a. Similarly, the parallax image generation section 15 acquires, from the image processing section 11b, a viewpoint image that has been imaged by the imaging section 21b and subjected to image processing by the image processing section 11b. Also, for each display section 30, the parallax image generation section 15 acquires information indicating the parallax value control result (that is, the parallax value controlled on the basis of the display conditions of that display section 30) from the parallax control section 13.

(Step S107)

The parallax image generation section 15 generates parallax images (that is, a right-eye image and a left-eye image) corresponding to each viewpoint of the user, on the basis of the viewpoint images corresponding to each of the viewpoints acquired from the image processing sections 11*a* and 11*b*, respectively, and the parallax value control result acquired for each display section 30.

(Step S109)

Subsequently, the parallax image generation section 15 generates what is called a multi-viewpoint image presented by the viewpoint images corresponding to each of the multiple viewpoints generated for each of the display section 30, on the basis of the parallax value control result, and causes the display section 30 to display the generated multi-viewpoint image.

(Step S111)

Note that in the case in which the viewing state (for example, the viewing distance L) or the imaging state (for example, the working distance w12 or the inter-optical-axis distance w11) changes (step S111, YES), the parallax control section 13 may also update the parallax value on the basis of the changed viewing state or imaging state. In this case, it is sufficient for the parallax image generation section 15 to execute the generation of each parallax image, and the generation and output of a multi-viewpoint image based on such parallax images, on the basis of the updated parallax value.

(Step S113)

Note that as long as the imaging state or the viewing state does not change (step S111, NO) and the end of image acquisition of the observation target M1 is not indicated (step S113, NO), the image processing device 10 sequentially executes each process related to the acquisition of input image data (step 105), the generation of a parallax images (step 107), and the generation and output of a multi-viewpoint image (step 109). Subsequently, in the case in which the end of image acquisition of the observation target M1 is indicated (step S113, YES), the image processing device 10 ends the series of operations.

The above thus references FIG. 16 to describe an example of the flow of a series of operations by the medical stereoscopic observation system according to the present embodiment, with particular focus on operations by the image processing device 10.

6. Modifications

Next, as modifications of the medical stereoscopic observation system according to the present embodiment, examples of the operations of the image processing device 10 in particular will be described.

[6.1. Modification 1: Example of Control in Association with Electronic Zoom]

Figure 17:
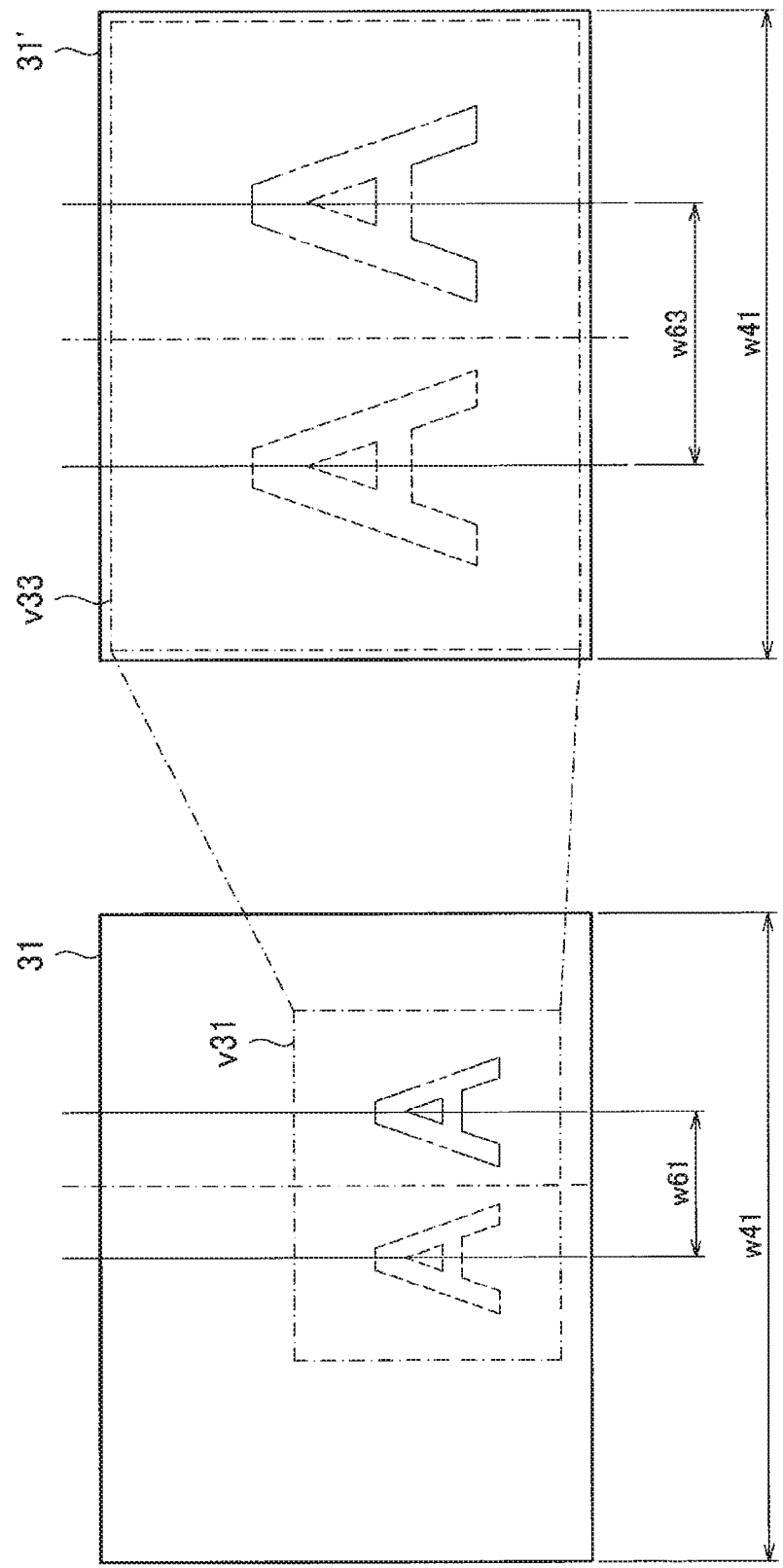
FIG. 17 is an explanatory diagram for explaining an example of operations by an image processing device according to Modification 1.
Figure 18:
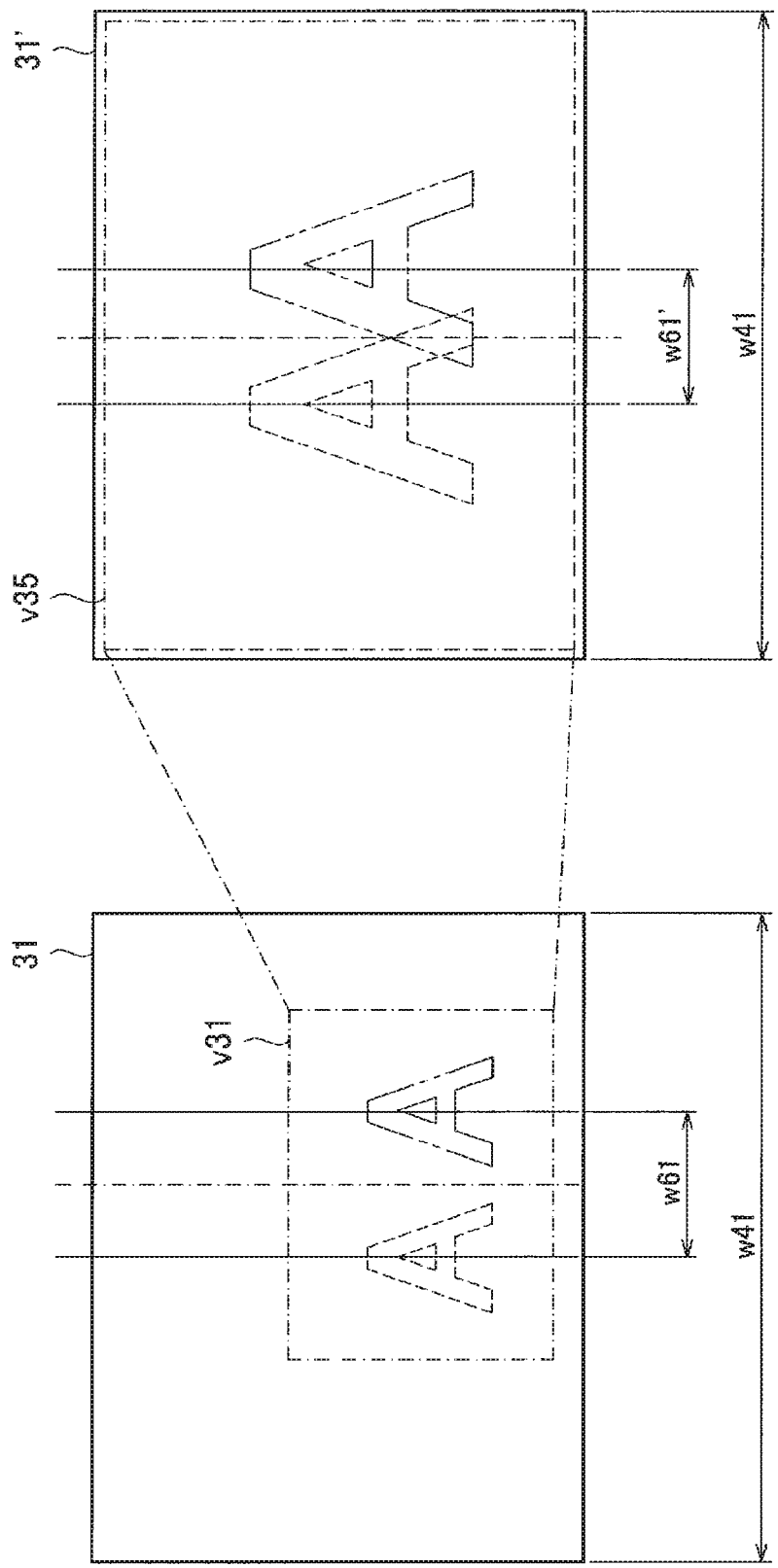
FIG. 18 is an explanatory diagram for explaining an example of operations by an image processing device according to Modification 1.

First, as Modification 1, FIGS. 17 and 18 will be referenced to describe an example of control of the parallax value by the image processing device 10 in the case of using electronic zoom to magnify (or reduce) a portion of a multi-viewpoint image generated on the basis of viewpoint images imaged by the imaging sections 21*a* and 21*b*. FIGS. 17 and 18 are explanatory diagrams for explaining an example of operations by the image processing device 10 according to Modification 1.

For example, FIG. 17 illustrates an example of a case of using electronic zoom to magnify and display a multi-viewpoint image displayed on the display section 30. In FIG. 17, the reference sign 31 schematically indicates the display screen of the display section 30 before magnifying the multi-viewpoint image. Also, the reference sign 31' schematically indicates the display screen of the display section 30 after magnifying the multi-viewpoint image. Also, the reference sign w41 indicates the horizontal width of the display screen of the display section 30 (that is, the display screens 31 and 31').

In the example illustrated in FIG. 17, among the multi-viewpoint image displayed on the display screen 31, the region indicated by the reference sign v31 is magnified and displayed by electronic zoom. Note that the reference sign v33 schematically indicates an example of a magnified image in the case of using electronic zoom to magnify the region v31 in the multi-viewpoint image before magnification. The reference sign w61 indicates the display spacing based on the parallax value between the respective parallax images displayed in the region v31 in the multi-viewpoint image before magnification by the electronic zoom. Also, the reference sign w63 schematically indicates the spacing between the respective parallax images (in other words, the display spacing based on the parallax value) in the magnified image v33, which corresponds to the display spacing w61 before magnification by the electronic zoom.

As illustrated in FIG. 17, if the multi-viewpoint image presented by the viewpoint images corresponding to each viewpoint is simply magnified by electronic zoom, the spacing between the parallax images (that is, the display spacing based on the parallax value) is also magnified. For this reason, in the multi-viewpoint image after magnification by the electronic zoom, the stereoscopic effect is strengthened compared to the multi-viewpoint image before magnification. Similarly, in the case of reduction by electronic zoom, the spacing between the parallax images is reduced, and the multi-viewpoint image after reduction has a weakened stereoscopic effect compared to the multi-viewpoint image before reduction.

In light of such circumstances, even in the case of presenting magnified display (or reduced display) by electronic zoom, the image processing device 10 according to Modification 1 enables observation of a three-dimensional image of an observation target with a similar stereoscopic effect, regardless of whether the image is before or after magnification (or before or after reduction).

Specifically, in the case in which magnification or reduction is performed by electronic zoom, the size in real space of the multi-viewpoint image displayed on the display section 30 (that is, the display size) changes. For this reason, in the case in which the display size changes due to a magnification or a reduction by electronic zoom, the image processing device 10 updates the parallax value on the basis of the changed display size.

For example, FIG. 18 is an explanatory diagram for explaining an example of control of the parallax value by the image processing device 10 according to Modification 1. Note that the contents indicated by the reference signs 31, 31', w41, v31, and w61 in FIG. 18 are similar to the case of FIG. 17. Also, the reference sign v35 schematically indicates an example of a multi-viewpoint image after magnification in the case in which the region v31 in the multi-viewpoint image before magnification in the example illustrated in FIG. 18 is magnified using electronic zoom by the image processing device 10 according to Modification 1. Also, the reference sign w61' schematically illustrates the spacing between the respective parallax images (that is, the display spacing based on the parallax value) in the multi-viewpoint image v35.

In the example illustrated in FIG. 18, the image processing device 10 controls the parallax value corresponding to the multi-viewpoint image v35 after magnification so that the display spacing w61' in the multi-viewpoint image v35 becomes approximately equal to the display spacing w61 in the multi-viewpoint image before magnification.

Specifically, the image processing device 10 computes the size in real space (that is, the display size) of the multi-viewpoint image v35 after magnification, on the basis of the size (number of inches) and resolution (number of pixels) of the display section 30, as well as the magnification ratio of the electronic zoom. The image processing device 10 controls the parallax value corresponding to the multi-viewpoint image v35 on the basis of the computed display size, so that the spacing between the respective parallax images when displaying the multi-viewpoint image v35 (that is, the display spacing w61') becomes approximately equal to the spacing between the respective parallax images in the multi-viewpoint image before magnification (that is, the display spacing w61).

Note that in the case in which the selectable magnification settings of the electronic zoom are predetermined, a parallax value corresponding to the magnification setting may also be computed in advance as a preset.

Next, the image processing device 10 magnifies each of the viewpoint images output from the image processing sections 11a and 11b with the electronic zoom, and generates a parallax image corresponding to each viewpoint on the basis of each of the magnified viewpoint images and the controlled parallax value (that is, the parallax value corresponding to the magnified image v35). The image processing device 10 generates a multi-viewpoint image presented by each of the generated parallax images on the basis of the controlled parallax value. Note that the multi-viewpoint image generated at this point corresponds to the multi-viewpoint image v35 after magnification illustrated in FIG. 18.

Subsequently, the image processing device 10 causes the generated multi-viewpoint image v35 to be displayed on the corresponding display section 30. Note that, as illustrated in FIG. 18, the display spacing w61' based on the parallax value of the multi-viewpoint image v35 displayed on the display section 30 at this point has been adjusted to be approximately equal to the display spacing w61 based on the parallax value in the multi-viewpoint image before magnification. With this arrangement, even in the case of presenting display magnified by electronic zoom, the user becomes able to observe a three-dimensional image of an observation target with a similar stereoscopic effect, regardless of whether the image is before or after magnification. Note that even in the case of presenting display reduced by electronic zoom, obviously it is sufficient to control the parallax value in accordance with the display size after reduction, similarly to the case of magnification.

The above thus references FIGS. 17 and 18 to describe, as Modification 1, an example of control of the parallax value by the image processing device 10 in the case of using electronic zoom to magnify or reduce a portion of a multi-viewpoint image generated on the basis of viewpoint images imaged by the imaging sections 21a and 21b.

[6.2. Modification 2: Example of Control in Association with Multi-Screen Display]

Figure 19:
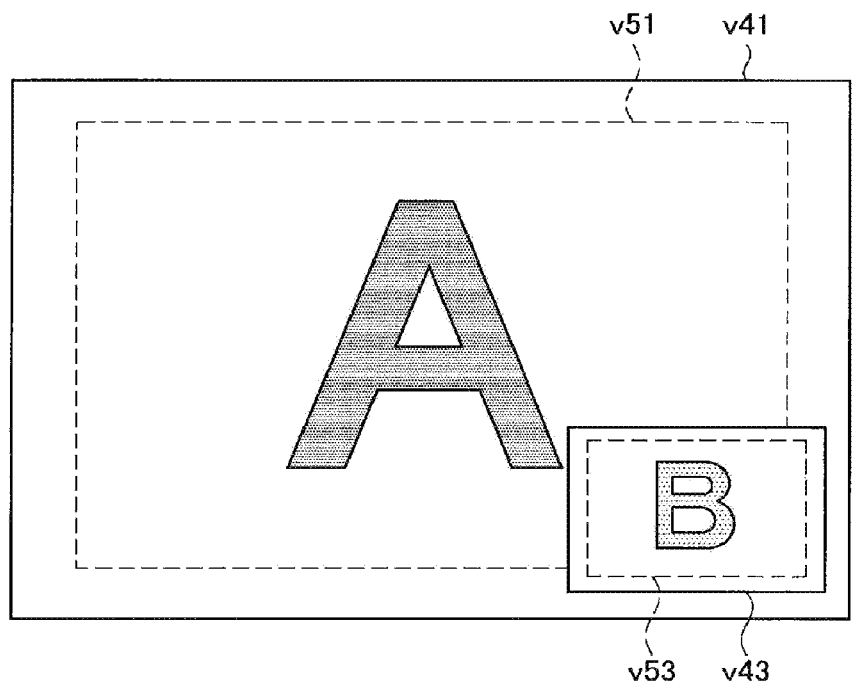
FIG. 19 is an explanatory diagram for explaining an example of operations by an image processing device according to Modification 2.
Figure 20:
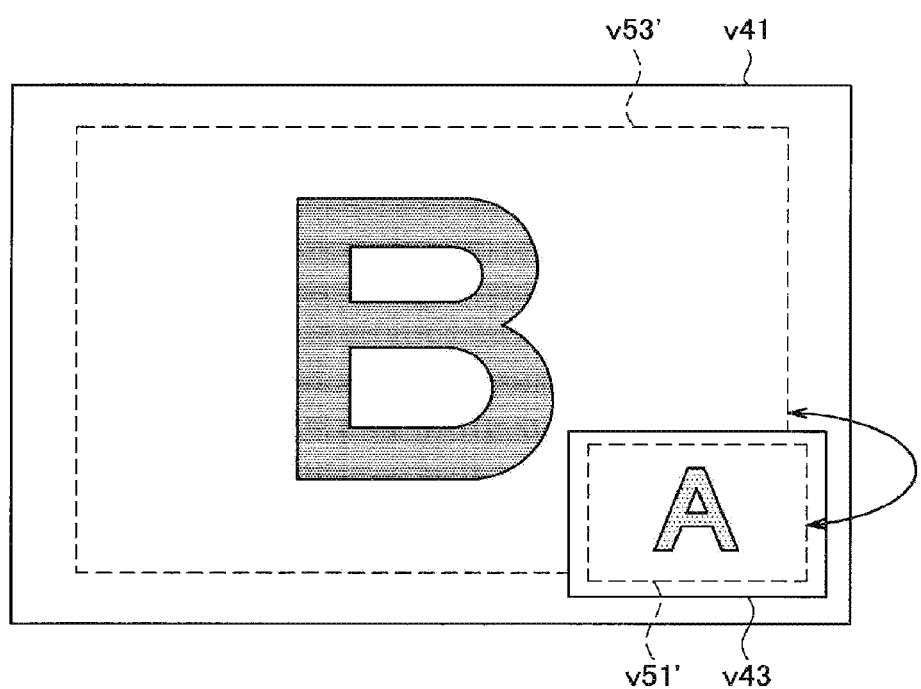
FIG. 20 is an explanatory diagram for explaining an example of operations by an image processing device according to Modification 2.

Next, as Modification 2, FIGS. 19 and 20 will be referenced to describe an example of control of the parallax value by the image processing device 10 in the case in which multiple screens (display regions) are presented on a single display section 30. FIGS. 19 and 20 are explanatory diagrams for explaining an example of operations by the image processing device 10 according to Modification 2.

The foregoing embodiment describes an example of control of the parallax value by the image processing device 10 in the case of displaying a multi-viewpoint image on multiple display sections 30 having different display conditions, the control being for presenting a three-dimensional image of the observation target M1 with a similar stereoscopic effect regardless of the differences in the display conditions.

On the other hand, in what is called an observation device, to enable the observation of multiple images by a single display section 30, in some cases multiple display regions are set within the screen displayed on the display section 30, and an image is displayed in each display region.

For example, the example illustrated in FIG. 19 illustrates an example of a case in which display regions v41 and v43 with different sizes are set within the screen of the display section 30. Note that in the example illustrated in FIG. 19, a multi-viewpoint image v51 is being displayed in the display region v41, while a multi-viewpoint image v53 is being displayed in the display region v43.

In the example illustrated in FIG. 19, the size in real space (that is, the display size) of the multi-viewpoint image v51 displayed on the display section 30 depends on the display conditions (for example, the size and resolution) of the display section 30, and the size of the display region v41 within the screen displayed on the display section 30. Similarly, the display size of the multi-viewpoint image v53 displayed on the display section 30 depends on the display conditions of the display section 30 and the size of the display region v43 within the screen displayed on the display section 30.

Herein, as described earlier, in the case in which the sizes of the display regions v41 and v43 are different, the sizes in real space (that is, the display sizes) of the display regions v41 and v43 are also different. For this reason, for example, even if multi-viewpoint images set with similar parallax values are displayed in both of the display regions v41 and v43, the display spacing based on the parallax value between the respective viewpoint images (that is, the right-eye image and the left-eye image) is different, and thus three-dimensional images with different stereoscopic effects will be observed by the user.

Given the above, in the case in which multiple display regions are presented on a single display section 30, as illustrated in FIG. 19, the image processing device 10 according to Modification 2 controls the parallax value of the multi-viewpoint image presented in each display region, in accordance with the display size of each display region. Note that the display size of each display region can be computed on the basis of the display conditions (that is, the size (number of inches) and resolution (number of pixels)) of the display section 30, and the size (that is, the relative extent) of each display region within the screen displayed on the display section 30.

By such a configuration, even under circumstances in which multi-viewpoint images are displayed in each of multiple display regions of different sizes presented on a single display section 30, the user becomes able to observe the multi-viewpoint image displayed in each display region with a similar stereoscopic effect.

Note that, as illustrated in FIG. 19, under circumstances in which multiple display regions of different sizes are presented on a single display section 30, a case may also be anticipated in which the images displayed in each of the display regions are exchanged where appropriate.

For example, the example illustrated in FIG. 20 illustrates an example of a case of exchanging and displaying the multi-viewpoint images v51 and v53 that had been displayed respectively in the display regions v41 and v43 in FIG. 19. In other words, in FIG. 20, the reference sign v51' indicates the multi-viewpoint image v51, which had been displayed in the display region v41 in FIG. 19, in the case of being displayed in the display region v43. Also, the reference sign v53' indicates the multi-viewpoint image v53, which had been displayed in the display region v43 in FIG. 19, in the case of being displayed in the display region v41.

In such a case, as illustrated in FIGS. 19 and 20, before and after the exchange of the multi-viewpoint images v51 and v53 displayed respectively in the display regions v41 and v43, the display sizes of the multi-viewpoint images v51 and v53 are changed.

For this reason, in association with the exchange of the multi-viewpoint images v51 and v53 displayed respectively in the display regions v41 and v43, the image processing device 10 may also control the parallax values for displaying each of the multi-viewpoint images, in accordance with the display sizes of the multi-viewpoint images v51' and v53' displayed after the exchange.

By such a configuration, even in the case of exchanging and displaying the multi-viewpoint images v51 and v53 that had been displayed respectively in the display regions v41 and v43, the user becomes able to observe each of the multi-viewpoint images with a similar stereoscopic effect, regardless of whether the images are before or after the exchange.

The above thus references FIGS. 19 and 20 to describe, as Modification 2, an example of control of the parallax value by the image processing device 10 in the case in which multiple screens (display regions) are presented on a single display section 30.

[6.3. Modification 3: Presentation of Field of View Range]

Figure 21:
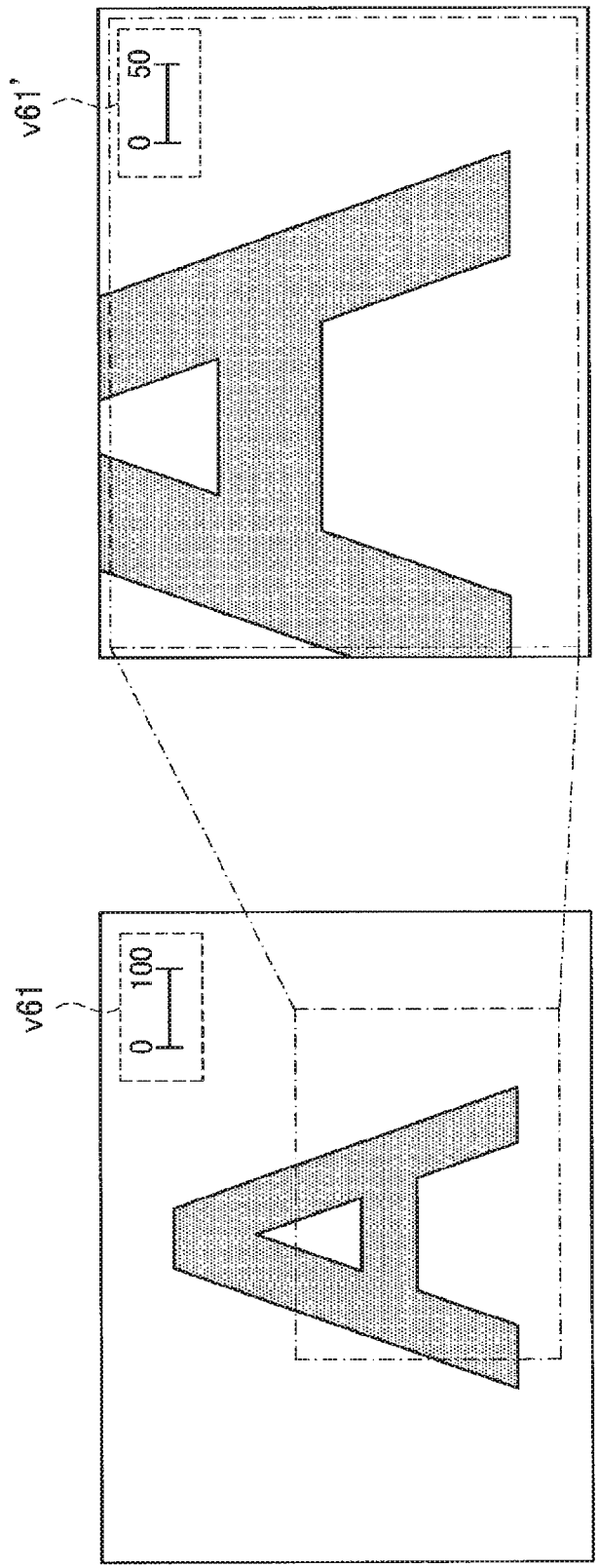
FIG. 21 is an explanatory diagram for explaining an overview of an image processing device according to Modification 3.

Next, FIG. 21 will be referenced to describe an image processing device 10 according to Modification 3. FIG. 21 is an explanatory diagram for explaining an overview of an image processing device 10 according to Modification 3.

As described above, in the case of displaying an image (for example, a multi-viewpoint image) on each of multiple display sections 30 of different size, the display size of the image is different in some cases, in accordance with the display conditions (the size (number of inches) and resolution (number of pixels)) of the display section 30 on which the image is displayed. Under such circumstances, in some cases the user may have difficulty recognizing the size in real space of the range imaged as the image (that is, the field of view range) or a subject displayed in the image (that is, the observation target).

In light of such circumstances, in the image processing device 10 according to Modification 3, display information indicating the size in real space (or an indicator indicating such a size) of the field of view range or the subject is presented inside the image to display (for example, a multi-viewpoint image). For example, in the example illustrated in FIG. 21, the image processing device 10 presents display information v61 indicating the size in real space of the field of view range imaged as the image.

In this case, for example, the image processing device 10 computes the size in real space of the range imaged as the image by the imaging sections 21a and 21b (that is, the field of view range), on the basis of parameters related to the imaging state by which the imaging sections 21a and 21b image the viewpoint images (that is, the inter-optical-axis distance and the working distance). In addition, at this point, the image processing device 10 may also compute the size in real space of the field of view range in accordance with the focus position of each of the imaging sections 21a and 21b, for example. Obviously, the example described above is merely one example, and the method is not particularly limited insofar as the image processing device 10 is capable of computing the size in real space of the field of view range.

Subsequently, in accordance with the computation result for the field of view range, the image processing device 10 generates display information v61 as illustrated in FIG. 21, for example, and may embed the display information v61 into the viewpoint images imaged by the imaging sections 21a and 21b (or into a multi-viewpoint image based on the viewpoint images).

By such a configuration, the user becomes able to recognize the size in real space of the field of view range imaged as the image or a subject in the image (that is, the observation target), through the display information v61 inside the image displayed on the display section 30.

Note that, as described in Modification 2, in the case of using electronic zoom to magnify and display an image on the display section 30, the size of the region displayed on the display section 30 from among the imaged image varies in some cases in accordance with the magnification of the electronic zoom. In such cases, the image processing device 10 may update the content of the information presented as the display information v61, in accordance with the size of the magnified image after magnification by the electronic zoom (in other words, the magnification of the electronic zoom).

For example, in FIG. 21, the reference sign v61' indicates an example of display information v61 presented on a magnified image after magnification by electronic zoom. In other words, the image illustrated on the right side of FIG. 21 illustrates a magnified image obtained by magnifying a portion of the image illustrated on the left side by a factor of 4 (a factor of 2 in the vertical direction and a factor of 2 in the horizontal direction). For this reason, in the example illustrated in FIG. 21, before and after magnification by the electronic zoom, the display information v61 and v61' are indicated at the same size on the display section 30, but the size in real space indicated by each piece of display information is different. For this reason, in the example illustrated in FIG. 21, the image processing device 10 exchanges the display content of each of the display information v61 and v61' in accordance with the size in real space.

In addition, the display information v61 and v61' illustrated in FIG. 21 is merely one example, and the display mode is not particularly limited insofar as the user is capable of recognizing the size in real space of the field of view range imaged as the image or a subject in the image (that is, the observation target).

The above thus references FIG. 21 to describe an image processing device 10 according to Modification 3.

[6.4. Modification 4: Control According to Viewing Distance]

Figure 22:
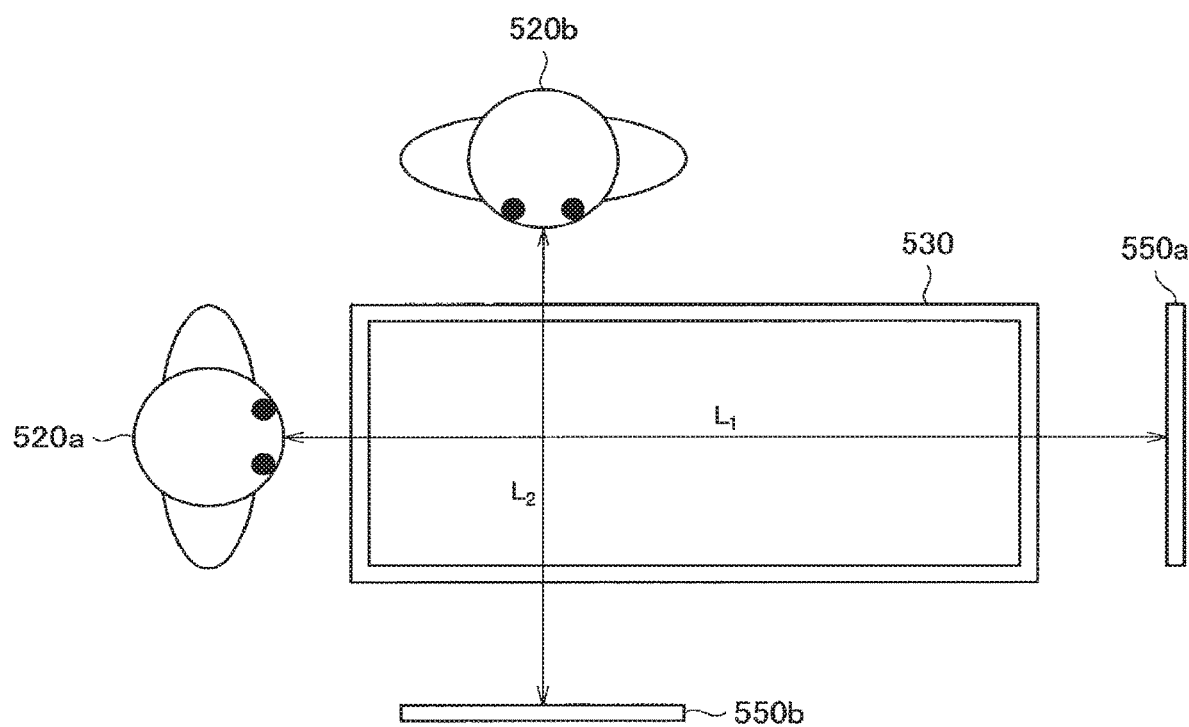
FIG. 22 is an explanatory diagram for explaining an overview of an image processing device according to Modification 4.

Next, FIG. 22 will be referenced to describe an image processing device 10 according to Modification 4. FIG. 22 is an explanatory diagram for explaining an overview of an image processing device 10 according to Modification 4. In Modification 4, an example of a case of controlling the parallax value in accordance with the viewing distance L will be described.

FIG. 22 illustrates an example of a case in which multiple users 520a and 520b are positioned in different places with respect to an operating table 530, and are performing work cooperatively while observing a 3D image of an observation target displayed on different display devices 550a and 550b. Note that in this description, the user 520a is observing a 3D image displayed on the display device 550a. Suppose that the viewing distance in this case is $L_1$. Also, the user 520b is observing a 3D image displayed on the display device 550b. Suppose that the viewing distance in this case is $L_2$.

Herein, in the case in which the viewing distances $L_1$ and $L_2$ exist in the relationship $L_1 \neq L_2$, the angle of convergence in the case of the user 520a viewing the 3D image displayed on the display device 550a is different from the angle of convergence in the case of the user 520b viewing the 3D image displayed on the display device 550b. For this reason, even in the case in which the sizes of the display screens are equal between the display devices 550a and 550b, in the case of displaying a 3D image set with the same parallax value on each of the display devices 550a and 550b, the users 520a and 520b will experience different stereoscopic effects.

In light of such circumstances, the image processing device 10 according to Modification 4 may control the parallax value of the 3D image to display on each display device, in accordance with the viewing distance corresponding to each of the display devices 550a and 550b.

For example, the image processing device 10 may control the parallax value of the 3D image displayed on each display device so that the angle of convergence in the case of the user 520a viewing the 3D image displayed on the display device 550a and the angle of convergence in the case of the user 520b viewing the 3D image displayed on the display device 550b become approximately equal.

Also, on the basis of the viewing distances $L_1$ and $L_2$, the image processing device 10 may respectively control the parallax value of the 3D image to display on each display device so that the oblateness θ1/θ2 becomes a value close to 1 for each of the display devices 550a and 550b. Also, on the basis of the viewing distances $L_1$ and $L_2$, the image processing device 10 may respectively control the parallax value of the 3D image to display on each display device so that the parallax angle becomes 1 degree (60 arc minutes) or less for each of the display devices 550a and 550b.

Note that the above describes an example of controlling the parallax value by focusing on only the viewing distances $L_1$ and $L_2$, but in the case in which the size of the display screen is different between the display devices 550a and 550b, obviously the control of the parallax value may be conducted in accordance with the size.

The above thus references FIG. 22 to describe an image processing device 10 according to Modification 4.

7. Hardware Configuration

Figure 23:
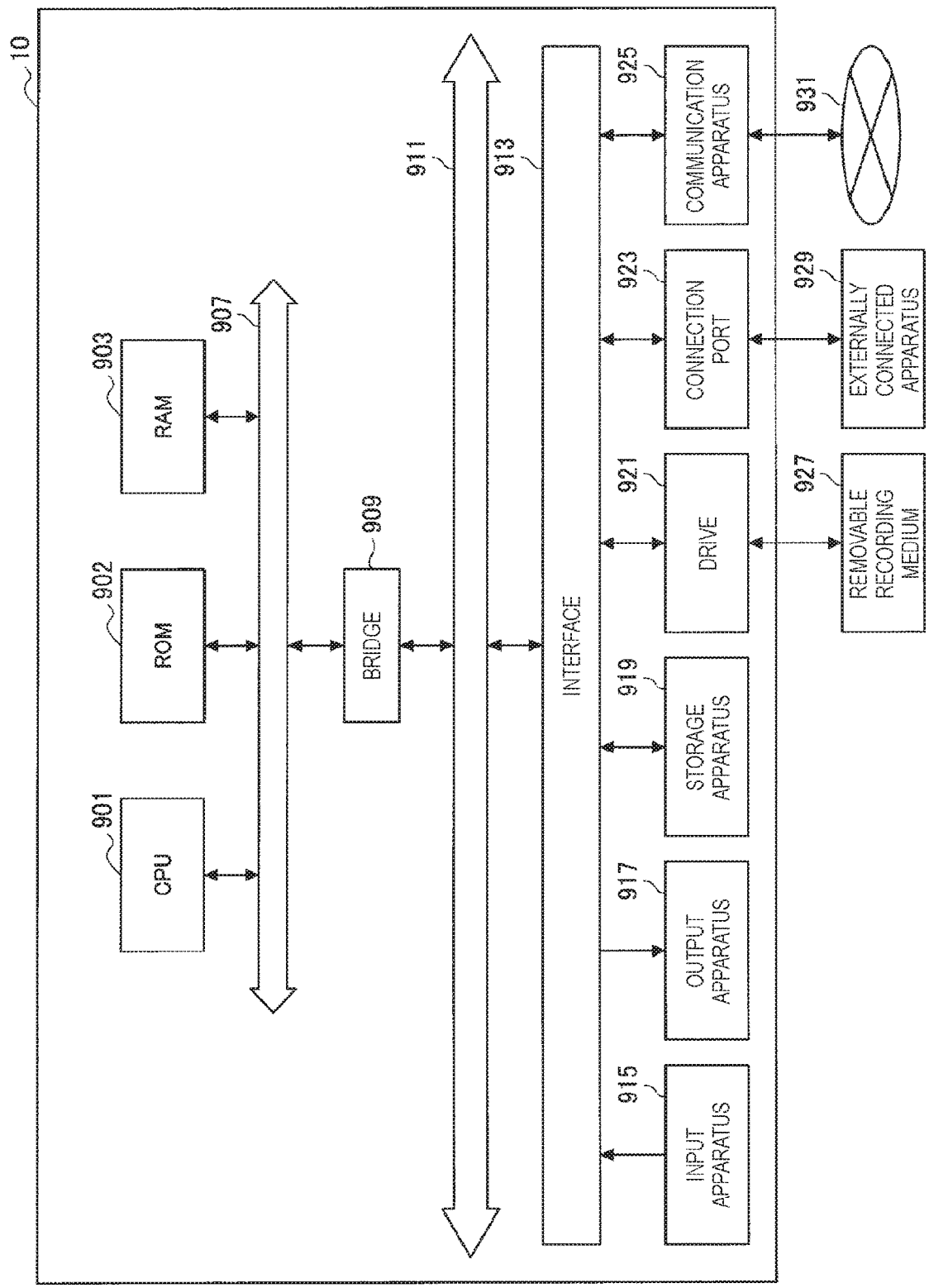
FIG. 23 is a function block diagram illustrating an example configuration of the hardware configuration of an information processing device constituting a medical stereoscopic observation system according to the embodiment.

Next, a hardware configuration of an information processing apparatus 900 constituting a medical stereoscopic observation system according to the present embodiment, such as the surgical video microscope device or the image processing device described earlier, will be described in detail with reference to FIG. 23. FIG. 23 is a function block diagram illustrating an example configuration of the hardware configuration of an information processing apparatus 900 constituting a medical stereoscopic observation system according to an embodiment of the present disclosure.

The information processing apparatus 900 constituting a medical stereoscopic observation system according to the present embodiment is equipped primarily with a CPU 901, ROM 903, and RAM 905. Additionally, the information processing apparatus 900 may also be equipped with a host bus 907, a bridge 909, an external bus 911, an interface 913, an input apparatus 915, an output apparatus 917, a storage apparatus 919, a drive 921, a connection port 923, and a communication apparatus 925.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like. Note that each configuration of each of the image processing apparatuses described earlier with reference to FIG. 16 may be realized by the CPU 901, for example.

The host bus 907 is connected to the external bus 911 such as a PCI (Peripheral Component Interconnect/Interface) bus via the bridge 909. Additionally, the input apparatus 915, the output apparatus 917, the storage apparatus 919, the drive 921, the connection port 923, and the communication apparatus 925 are connected to the external bus 911 via the interface 913.

The input apparatus 915 is an operation mechanism operated by a user, such as a mouse, a keyboard, a touch panel, buttons, a switch, a lever, or a pedal. Also, the input apparatus 915 may be a remote control mechanism (a so-called remote control) using, for example, infrared light or other radio waves, or may be an externally connected apparatus 929 such as a mobile phone or a PDA conforming to the operation of the information processing apparatus 900. Furthermore, the input apparatus 915 generates an input signal based on, for example, information which is input by a user with the above operation mechanism, and is configured from an input control circuit for outputting the input signal to the CPU 901. The user of the information processing apparatus 900 can input various data to the information processing apparatus 900 and can instruct the information processing apparatus 900 to perform processing by operating this input apparatus 915. Note that the operation section 50 described earlier with reference to FIG. 15 may be realized by the input apparatus 915.

The output apparatus 917 is configured from a device capable of visually or audibly notifying acquired information to a user. Examples of such device include display apparatuses such as a CRT display apparatus, a liquid crystal display apparatus, a plasma display apparatus, an EL display apparatus and lamps, audio output apparatuses such as a speaker and a headphone, a printer, and the like. For example, the output apparatus 917 outputs a result obtained by various processing performed by the information processing apparatus 900. More specifically, the display apparatus displays, in the form of texts or images, a result obtained by various processes performed by the information processing apparatus 900. On the other hand, the audio output apparatus converts an audio signal such as reproduced audio data and sound data into an analog signal, and outputs the analog signal. Note that each of the display sections 30a and 30b described earlier with reference to FIG. 15 may be realized by the output apparatus 917.

The storage apparatus 919 is a device for storing data configured as an example of a storage unit of the information processing apparatus 900 and is used to store data. The storage apparatus 919 is configured from, for example, a magnetic storage apparatus such as a HDD (Hard Disk Drive), a semiconductor storage apparatus, an optical storage apparatus, or a magneto-optical storage apparatus. This storage apparatus 919 stores programs to be executed by the CPU 901, and various data.

The drive 921 is a reader/writer for recording medium, and is embedded in the information processing apparatus 900 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (a registered trademark) medium. The removable recording medium 927 may be a CompactFlash (CF; a registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing apparatuses to directly connect to the information processing apparatus 900. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (a registered trademark) (High-Definition Multimedia Interface) port, and the like. By the externally connected apparatus 929 connecting to this connection port 923, the information processing apparatus 900 directly obtains various data from the externally connected apparatus 929 and provides various data to the externally connected apparatus 929.

The communication apparatus 925 is a communication interface configured from, for example, a communication apparatus for connecting to a communication network 931. The communication apparatus 925 is, for example, a wired or wireless LAN (Local Area Network), Bluetooth (registered trademark), a communication card for WUSB (Wireless USB), or the like. Alternatively, the communication apparatus 925 may be a router for optical communication, a router for ADSL (Asymmetric Digital Subscriber Line), a modem for various communications, or the like. This communication apparatus 925 can transmit and receive signals and the like in accordance with a predetermined protocol such as TCP/IP on the Internet and with other communication apparatuses, for example. The communication network 931 connected to the communication apparatus 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the information processing apparatus 900 constituting a medical stereoscopic observation system according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment. Note that, although not illustrated in FIG. 23, the various structural elements corresponding to the information processing apparatus 900 constituting a medical stereoscopic observation system (in other words, a surgical video microscope device or an image processing device) obviously are provided.

Note that it is also possible to develop a computer program for realizing the respective functions of the information processing apparatus 900 constituting a medical stereoscopic observation system according to the present embodiment as described above, and implement the computer program in a personal computer or the like. In addition, a computer-readable recording medium storing such a computer program may also be provided. The recording medium may be a magnetic disc, an optical disc, a magneto-optical disc, or flash memory, for example. Furthermore, the above computer program may also be delivered via a network, for example, without using a recording medium.

8. Conclusion

As described above, in a medical stereoscopic observation system according to the present embodiment, an image processing device 10 computes the display size of an image (for example, a multi-viewpoint image) displayed on a display section 30, on the basis of the display conditions (for example, the size (number of inches) and resolution (number of pixels)) of the display section 30. Next, the image processing device 10 controls a parallax value corresponding to the display section 30 on the basis of the display size computed for each display section 30. Subsequently, for each display section 30, the image processing device 10 generates a multi-viewpoint image presented by viewpoint images corresponding to respective viewpoints on the basis of the parallax value control result, and causes the corresponding display section 30 to display the multi-viewpoint image.

By such a configuration, even under circumstances in which a user observes a three-dimensional image of an observation target via each of multiple display sections 30a and 30b having different display conditions such as size (number of inches) and resolution (number of pixels), the user becomes able to observe the observation target with a similar stereoscopic effect, regardless of the differences in the display conditions.

Note that although the example described above illustrates an example of controlling the parallax value so that the observation target is observed with a similar stereoscopic effect between multiple different display sections 30 (or display regions) with different display conditions, the content of the control of the parallax value by the image processing device 10 is not necessarily limited to the same mode. In other words, insofar as the parallax value of a multi-viewpoint image displayed on the display section 30 is controlled in accordance with display size computed on the basis of the display conditions of the display section 30, the content of the control of the parallax value is not particularly limited.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical stereoscopic observation device including:

an acquisition section that acquires input image data;

a parallax control section that controls, for each of a plurality of different display regions, a parallax value in accordance with display size of the display region; and an image generation section that generates, for each display region, a parallax image corresponding to each of a plurality of viewpoints for display in the display region, on a basis of the acquired input image data and the parallax value corresponding to the display region.

(2)

The medical stereoscopic observation device according to (1), in which the image generation section generates, for a display region on each of a plurality of display sections, the parallax image corresponding to each of a plurality of viewpoints for display in the display region.

(3)

The medical stereoscopic observation device according to (2), in which the parallax control section computes the display size of the display region presented on the display section, on a basis of size of the display section and resolution of the display section.

(4)

The medical stereoscopic observation device according to (3), in which the parallax control section acquires at least one of information indicating the size of the display section and information indicating the resolution of the display section from the display section.

(5)

The medical stereoscopic observation device according to any one of (1) to (4), in which the parallax control section controls, for each of a plurality of display regions presented on a common display section, the parallax value in accordance with display size in the display region, and the image generation section generates, for display in each of the plurality of display regions, the parallax image corresponding to each of a plurality of viewpoints, on a basis of the parallax value corresponding to the display region.

(6)

The medical stereoscopic observation device according to any one of (1) to (5), in which the parallax control section controls the parallax value corresponding to the display region, on a basis of a ratio between an inward angle formed between an observation target, and each of a plurality of viewpoints from which an imaging section images an image of the observation target, and an angle of convergence formed between a position of an image made to be observed by a user by the plurality of parallax images displayed in the display region, and viewpoint positions corresponding to a right eye and a left eye of the user.

(7)

The medical stereoscopic observation device according to any one of (1) to (6), in which the parallax control section controls the parallax value corresponding to the display region on a basis of a difference between a first angle of convergence formed between a position of an image made to be observed by a user by the plurality of parallax images displayed in the display region, and viewpoint positions corresponding to a right eye and a left eye of the user, and a second angle of convergence formed between a position on the display region, and the viewpoint positions corresponding to the right eye and the left eye of the user.

(8)

The medical stereoscopic observation device according to any one of (1) to (6), in which the parallax control section controls the parallax value corresponding to the display region in accordance with magnification of electronic zoom for magnified or reduced display of the parallax image in the display region.

(9)

The medical stereoscopic observation device according to any one of (1) to (8), in which the parallax control section controls the parallax value corresponding to each of the plurality of display regions in accordance with a change of a distance between an observation target, and an imaging section that images an image of the observation target.

(10)

The medical stereoscopic observation device according to any one of (1) to (9), in which the parallax control section controls the parallax value corresponding to the display region in accordance with a change of the display size of the display region, and the image generation section updates the parallax image for display in the display region on a basis of a control result of the parallax value.

(11)

A medical stereoscopic observation method including:

acquiring input image data;

controlling, for each of a plurality of different display regions, a parallax value in accordance with display size of the display region; and generating, for each display region, a parallax image corresponding to each of a plurality of viewpoints for display in the display region, on a basis of the acquired input image data and the parallax value corresponding to the display region.

(12)

A program causing a computer to execute:

acquiring input image data;

controlling, for each of a plurality of different display regions, a parallax value in accordance with display size of the display region; and generating, for each display region, a parallax image corresponding to each of a plurality of viewpoints for display in the display region, on a basis of the acquired input image data and the parallax value corresponding to the display region.

REFERENCE SIGNS LIST 10 image processing device
11a, 11b image processing section
13 parallax control section
15 parallax image generation section
20 imaging unit
21a, 21b imaging section
23 optical system
30 display section
40 control section
50 operation section

The invention claimed is:

1. A medical stereoscopic observation device comprising:
circuitry configured to:
acquire input image data;
control, for each of a plurality of different display regions, a parallax in accordance with display size of the display region and parameters related to an imaging state including a change in a working distance between an observation target and an imaging section for imaging the observation target; and
generate, for each display region, a parallax image corresponding to each of a plurality of viewpoints for display in the display region based the acquired input image data in the parallax corresponding to the display region.

2. The medical stereoscopic observation device according to claim 1, wherein the circuitry is further configured to generate, for a display region on each of a plurality of display sections, the parallax image corresponding to each of the plurality of viewpoints for display in the display region.

3. The medical stereoscopic observation device according to claim 2, wherein the circuitry is further configured to compute the display size of the display region presented on the display section based on a size of the display section and a resolution of the display section.

4. The medical stereoscopic observation device according to claim 3, wherein the circuitry is further configured to acquire at least one of information indicating the size of the display section and information indicating the resolution of the display section from the display section.

5. The medical stereoscopic observation device according to claim 1, wherein the circuitry is further configured to:
control, for each of a plurality of display regions presented on a common display section, the parallax in accordance with display size in the display region, and
generate, for display in each of the plurality of display regions, the parallax image corresponding to each of the plurality of viewpoints based on the parallax corresponding to the display region.

6. The medical stereoscopic observation device according to claim 1, wherein the circuitry is further configured to control the parallax corresponding to the display region based on a ratio between an inward angle formed between a first set of rays extending from the observation target to each of a plurality of viewpoints from which the imaging section images an image of the observation target, and an angle of convergence formed between a second set of rays extending from a position of an image made to be observed by a user by the plurality of parallax images displayed in the display region to viewpoint positions corresponding to a right eye and a left eye of the user.

7. The medical stereoscopic observation device according to claim 1, wherein the circuitry is further configured to control the parallax corresponding to the display region based on a difference between a first angle of convergence formed between a first set of rays extending from a position of an image made to be observed by a user by the plurality of parallax images displayed in the display region to viewpoint positions corresponding to a right eye and a left eye of the user, and a second angle of convergence formed between a second set of rays extending from a position on the display region to the viewpoint positions corresponding to the right eye and the left eye of the user.

8. The medical stereoscopic observation device according to claim 1, wherein the circuitry is further configured to control the parallax corresponding to the display region in accordance with magnification of electronic zoom for magnified or reduced display of the parallax image in the display region.

9. The medical stereoscopic observation device according to claim 1, wherein the circuitry is further configured to control the parallax corresponding to each of the plurality of display regions in accordance with a change of a distance between the observation target, and the imaging section that images an image of the observation target.

10. The medical stereoscopic observation device according to claim 1, wherein the circuitry is further configured to:
control the parallax corresponding to the display region in accordance with a change of the display size of the display region, and
update the parallax image for display in the display region based on a control result of the parallax.

11. A medical stereoscopic observation method comprising:
acquiring input image data;
controlling, for each of a plurality of different display regions, a parallax in accordance with display size of the display region and parameters related to an imaging state including a change in a working distance between an observation target and an imaging section for imaging the observation target;
generating, for each display region, a parallax image corresponding to each of a plurality of viewpoints for display in the display region based on the acquired input image data in the parallax corresponding to the display region.

12. A non-transitory computer-readable medium storing instructions that, when executed by one or more processors of a device, cause the device to:
acquire input image data;
control, for each of a plurality of different display regions, a parallax in accordance with display size of the display region and parameters related to an imaging state including a change in a working distance between an observation target and an imaging section for imaging the observation target;
generate, for each display region, a parallax image corresponding to each of a plurality of viewpoints for display in the display region based on the acquired input image data in the parallax corresponding to the display region.

* * * * *